United States Patent [19]
Makovetsky et al.

[11] Patent Number: 5,929,181
[45] Date of Patent: Jul. 27, 1999

[54] METHOD FOR PREPARATION OF COPOLYMERS OF ETHYLENE/NORBORNENE-TYPE MONOMERS WITH NICKEL CATALYSTS

[75] Inventors: Kiryll Lvovich Makovetsky; Eugeny Shmerovich Finkelshtein; Viktor Ivanovich Bykov; Andrey Khristoforovich Bagdasaryan, all of Moscow, Russian Federation; Brian Leslie Goodall, Akron; Larry Funderburk Rhodes, Silver Lake, both of Ohio

[73] Assignees: The B.F.Goodrich Co., Richfield, Ohio; A.V. Topchiev Institute of Petrochemical Synthesis, A.V.Topchiev, Russian Federation

[21] Appl. No.: 08/871,245

[22] Filed: Jun. 9, 1997

[51] Int. Cl.$^6$ .................. C08F 232/08; C08F 210/02; C08F 4/80

[52] U.S. Cl. .................. 526/171; 526/161; 526/169.1; 526/172; 526/179; 526/281; 526/282; 526/279; 526/348

[58] Field of Search .................. 526/171, 160, 526/161, 172, 281, 348

[56] References Cited

U.S. PATENT DOCUMENTS

| | | |
|---|---|---|
| 3,330,815 | 7/1967 | McKeon et al. . |
| 3,644,564 | 2/1972 | Van Zwet et al. . |
| 3,657,204 | 4/1972 | Cesca et al. . |
| 3,661,803 | 5/1972 | Bauer et al. . |
| 3,686,351 | 8/1972 | Mason . |
| 4,948,856 | 8/1990 | Minchak et al. . |
| 5,468,819 | 11/1995 | Goodall .................. 526/171 |
| 5,569,730 | 10/1996 | Goodall et al. . |
| 5,677,405 | 10/1997 | Goodall et al. . |
| 5,714,556 | 2/1998 | Johnson .................. 526/135 |

FOREIGN PATENT DOCUMENTS

| | | |
|---|---|---|
| 0445755 | 9/1991 | European Pat. Off. . |
| 0504418 | 9/1992 | European Pat. Off. . |
| 0291970 | 9/1993 | European Pat. Off. . |
| 1364870 | 8/1974 | United Kingdom . |
| 9623010 | 8/1996 | WIPO . |
| 9637526 | 11/1996 | WIPO . |

OTHER PUBLICATIONS

Paper, in German, presented at meeting of the GDCh–Fachgruppe on "Progress in Polymer Synthesis" in Bad Nauheim (Germany), Mar. 21–22, 1994.

"Preparation and Reactivity Studies of Highly Versatile, Nickel–Based Polymerization Catalyst Systems", by Timothy J. Demig and Bruce M. Novak (Communications to the Editor, Macromolecules 1993, 26, 7089–7091).

"Stereospecific Polymerization of Butadiene by Catalysts Prepared from Allyl Nickel Halides", by L. Porri, G. Natta, and M.C. Gallazzi (Journal of Polymer Science: Part C No. 16 (1967).

"The Organic Chemistry of Nickel", by P.W. Jolly and G. Wilke (Organometallic Chemistry—A Series of Monographs, vol. 1 Organonickel Complexes) 1974.

"Reactions of Electrophilic Transition Metal Cations With Olefins and Small Ring Compounds. Rearrangements and Polymerization", by Ayusman Sen, Ta–Wang Lai and Richard R. Thomas (Journal of Organometallic Chemistry (1988)).

"The $Pd^{2+}$–catalyzed Polymerization of Norbornene", by Christof Mehler and Wilhelm Risse (Makromol. Chem., Rapid Commun.) Jan. 8, 1991.

"Pd(II)–catalyzed Polymerization of Norbornene Derivatives", by Christof Mehler (Makromol. Chem., Rapid Commun.) Jun. 4, 1992.

"Ethylene Homopolymerization With P,O–Chelated Nickel Catalysts", by U. Klabunde, R. Mulhaupt, T. Herskovitz, A.H. Janowicz, J. Calabrese and S.D. Ittel (Journal of Polymer Science: Part A: Polymer Chemistry, vol. 25 (1987).

"Effect of Unsaturated Hydrocarbons on the Polymerization of Butadiene with Nickel Catalyst", by Ryozo Sakata, Junichi Hosono, Akira Onishi, and Kenichi Ueda (Die Makromolekulars Chemie 139 (1970) 73–81 (Nr. 3333 ) Sep. 29, 1969.

"Homogeneous Catalysis—The Applications and Chemistry of Catalysis By Soluble Transition Metal Complexes", by George W. Parshall and Steven D. Ittel (Central Research and Development E.I. du Pont de Nemours and Company, A Wiley–Interscience Publication) 1992.

(List continued on next page.)

*Primary Examiner*—Fred Zitomer
*Attorney, Agent, or Firm*—Nestor W. Shust

[57] ABSTRACT

A method of preparing amorphous copolymers of ethylene and at least one norbornene (NB)-type comonomer is disclosed. These polymers may be random or alternating depending on the choice of catalyst and/or the relative ratio of the monomers used. This method comprises polymerizing said monomers in a diluent or in bulk in the presence of a neutral nickel catalyst which may be represented by the formula

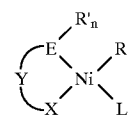

wherein Y may be a saturated or unsaturated hydrocarbyl chain, X may be oxygen or sulfur, E may be phosphorus, arsenic, antimony, oxygen or nitrogen, R and R' independently each is hydrogen or a hydrocarbyl group, L is a ligand containing a heteroatom P, N or O or L and R together with L may form part of a chelating structure in which case L is an ethylenic double bond.

26 Claims, No Drawings

OTHER PUBLICATIONS

"Crystal Structure of $(\eta^3$–syn–crotyl)–$\eta^7$–cycloota–1,5–diene)–nickel(II) hexafluophosphate,$Ni(C_8H_{12})(C_4H_7)P\ F_6$", by R. Kempe, J. Siele, S. Wache and R. Taube (1992)r.

"($\eta^3$–Allyl)palladium(II) and Palladium(II) Nitrile Catalysts for the Addition Polymerization of Norbornene Derivatives with Functional Groups", by Joice P. Mathew, Annette Reinmuth, Jennifer Melia, Noeleen Swords, and Wilhelm Risse (Macromolecules) 1996.

"($\eta^3$–Allyl)palladium(II) catalysts for the addition of polymerization of norbornene derivatives with functional groups", by Annette Reinmuth, Joice P. Mathews, Jennifer Melia, and Wilhelm Risse (Macromol, Rapid Commun. 17, 173–180) 1996.

La Chimica e L'Industria,(vol. 46, No. 4,, 428–429) 1964.

"Vinylic Polymerization of Norbornene by Pd(II)–Catalysis the Presence of Ethylene", by T.F.A. Haselwander, W. Heitz, M. Maskos, (Macromolecular Rapid Communication, 18, No. 8, 625–754) 1997.

"Cycloolefin–Copolymers: A New Class of Transparent Thermoplastics", by H. Cherdron, M.J. Brekner, F. Osan (Die Agnew. Chem. 223, 121–133) 1994.

METHOD FOR PREPARATION OF COPOLYMERS OF ETHYLENE/NORBORNENE-TYPE MONOMERS WITH NICKEL CATALYSTS

BACKGROUND OF THE INVENTION

This invention is directed to a method of copolymerizing ethylene with cycloolefin monomers, often referred to as norbornene-type, or NB-type. More specifically, the method employs neutral nickel catalysts and the polymers obtained by the method of this invention are amorphous addition copolymers which may be random or alternating in character.

Addition copolymers of ethylene and norbornene-type monomers are well known and can be prepared using a variety of catalysts disclosed in the prior art. This general type of copolymers can be prepared using free radical catalysts disclosed in U.S. Pat. No. 3,494,897 (Reding et al.); titanium tetrachloride and diethylaluminum chloride as disclosed in East German Patents 109,224 and 222,317 (VEB Leuna); or a variety of vanadium compounds, usually in combination with organoaluminum compounds, as disclosed in European Patent Application No. 156464 (Kajiura et al.). The copolymers obtained with these catalysts are random copolymers. U.S. Pat. No. 4,948,856 issued to Minchak et al. (B.F.Goodrich) discloses preparing generally alternating copolymers by the use of vanadium catalysts which are soluble in the norbornene-type monomer and a co-catalyst which may be any alkyl aluminum halide or alkylalkoxy aluminum halide. European Patent Application No. 0 504 418 A1 (Matsumoto et al.) discloses copolymerization of said monomers in the presence of catalysts such as transition metal compounds, including nickel compounds, and a compound which forms an ionic complex with the transition metal compound or a catalyst comprising said two compounds and an organoaluminum compound. More recently, metallocene catalysts were used to prepare copolymers of cycloolefins and α-olefins as disclosed in EP 283,164 (1987) issued to Mitsui Petrochemicals and EP 407,870 (1989), EP 485,893 (1990) and EP 503,422 (1991) issued to Hoechst AG. Most recently PCT published application WO96/23010 discloses processes of polymerizing ethylene, α-olefins and/or selected cyclic olefins which are catalyzed by selected transition metal compounds, including nickel complexes of diimine ligands, and sometimes also a cocatalyst. This disclosure provides, however, that when norbornene or a substituted norbornene is used, no other olefin can be present.

SUMMARY OF THE INVENTION

It is a general object of the invention to provide a novel method of preparing amorphous copolymers of ethylene and at least one norbornene (NB)-type comonomer. These polymers may be random or alternating depending on the choice of catalyst and/or the relative ratio of the monomers used. This method comprises polymerizing said monomers in a diluent or in bulk in the presence of a neutral nickel catalyst which may be represented by the formula

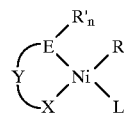

wherein Y may be a saturated or unsaturated hydrocarbyl chain, X may be oxygen or sulfur, E may be phosphorus, arsenic, antimony, oxygen or nitrogen, R and R' independently each is hydrogen or a hydrocarbyl group, L is a ligand containing a heteroatom P, N or O or L and R together with L may form part of a chelating structure in which case L is an ethylenic double bond.

DETAILED DISCLOSURE OF THE INVENTION

This invention is directed to a new method of preparing substantially amorphous copolymers of ethylene and one or more norbornene (NB)-type comonomers. The resulting copolymers may be alternating or random, depending on the relative proportion of each type of monomer used. This method comprises copolymerizing said monomers in the presence of a catalyst which is a neutral nickel compound bearing a bidentate ligand which chelates the nickel via two hetero-atoms (which may be the same or different) and a hydrocarbyl group (R) or a hydride.

Catalysts employed in the method of this invention may be represented by the formula

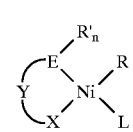

wherein Y is a saturated or unsaturated hydrocarbyl chain containing 1 to 3 carbon atoms which may be unsubstituted or substituted with hydrocarbyl groups having up to 20 carbon atoms or functional groups or two adjoining carbon atoms of said hydrocarbyl chain may form part of a cyclic structure, or said hydrocarbyl group may contain a hetero atom;

X is O or S;

E is P, As, Sb, N or O;

R and R' independently is H or $C_{1\text{-}20}$ hydrocarbyl group;

n is 0, 1 or 2, and

L is a ligand bearing the heteroatom P, N or O or alternatively L together with R form part of a chelating structure containing a nickel-carbon bond and a neutral two-electron donor moiety. Such a chelating structure would include, for example, where L is a C=C double bond, a ketone, aldehyde, an amide and the like.

Preferably L is a weakly coordinating ligand such as pyridine or a C=C double bond, E is phosphorus (P), X is oxygen (O) and Y is a hydrocarbyl chain containing 2 or 3 carbon atoms.

These catalysts can be prepared in advance or may be generated in situ by mixing the ligand with a suitable nickel complex such as bis (cyclooctadiene) nickel.

The above formula I, which broadly represents the catalysts useful in the method of this invention, includes the below identified sub-categories of such catalysts. These neutral nickel-containing catalysts consist essentially of one or more of the following:

1(a) A dinickel compound of the formula

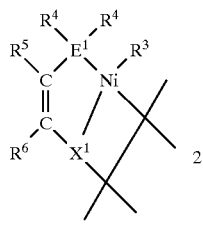

II wherein:
$R^3$ and each $R^4$, independently, is H or $C_{1-20}$ hydrocarbyl;
$X^1$ is O or S;
$E^1$ is P, As or Sb; and
$R^5$ and $R^6$, independently, is H, $C_{1-20}$ hydrocarbyl or a functional group selected from $-OR^2$, $-Cl$, $-CO_2R^2$, $-CO_2M$, $-C(O)N(R^1)_2$, $-C(O)R^2$, $-SR^2$, $-SO_2R^2$, $-SOR^2$, $-O-SO_2R^2$, $-P(O)(OR^2)_{2-y}(R^1)_y$, $-CN$, $-NHR^2$, $-N(R^2)_2$,

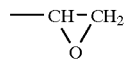

$-Si(OR^1)_{3-x}(R^1)_x$, $-OSi(OR^1)_{3-x}(R^1)_x$, $-NO_2$, $-SO_3M$, $-PO_3M_2$ and $-P(O)(OR^2)_2M$, wherein M is alkali or alkaline earth metal, ammonium, quaternary ammonium, phosphonium or arsonium, y is 0, 1 or 2, each $R^1$, independently, is H or $C_{1-20}$ hydrocarbyl, each $R^2$, independently, is $C_{1-20}$ hydrocarbyl, and x is 0 or an integer of 1 to 3, or $R^5$ and $R^6$, taken together with the carbon atoms to which they are attached, is a substituted or unsubstituted $C_{5-8}$ alicyclic, $C_{5-8}$ heterocyclic or C6-14 aromatic ring, the heteroatom of the heterocyclic ring being selected from O, N and S.

1(b) a nickel compound of the formula

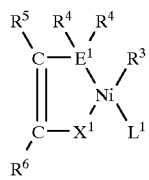

III wherein:
$R^3$, $R^4$, $R^5$, $R^6$, $X^1$ and $E^1$ are defined as above and $L^1$ is a weakly coordinating ligand, or $R^3$ and $L^1$ taken together form a group having the structure

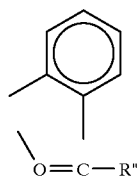

wherein R" is H, $C_{1-20}$ hydrocarbyl or oxyhydrocarbyl or $N(R^2)_2$ wherein each $R^2$, independently, is $C_{1-20}$ hydrocarbyl;

1 (c) a nickel compound of the formula

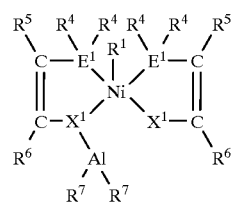

IV wherein:
$R^1$, $R^4$, $R^5$, $R^6$, $X^1$ and $E^1$ are as defined above; each $R^7$, independently, is H, $-OSi(R''')_3$, $C_{1-20}$ alkyl or oxyalkyl, $C_{6-20}$ aryl, alkaryl, aralkyl or oxyaryl, $-N(R^2)_2$ wherein $R^2$ is as defined above, or halogen, or both $R^7$ groups, taken together, form a 5 to 8-membered heterocyclic ring wherein the heteroatom is selected from O, N and S; and
each R''', independently, is $C_{1-20}$ alkyl or oxyalkyl, $C_{6-20}$ aryl, alkaryl, aralkyl or oxyaryl;
(2) a mixture comprising:
(i) a nickel compound of the formula

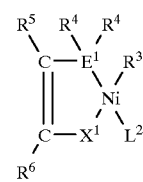

V wherein $R^3$, $R^4$, $R^5$, $R^6$, $X^1$ and $E^1$ are defined as above and $L^2$ is a strongly coordinating ligand; and
(ii) an acceptor compound which can react with $L^2$; and
(3) the mixture comprising:
(i) a nickel compound of the formula

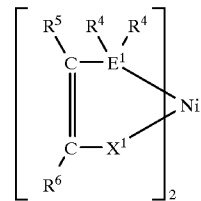

VI wherein $R^4$, $R^5$, $R^6$, $X^1$ and $E^1$ are defined as above; and
(ii) a suitable alkylating or arylating compound.
(4) a nickel compound of the formula:

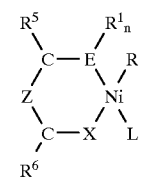

VII where E, X, R, L and n are as defined above, Z is a double bond or a carbon atom containing one hydrogen or fluorine or one or two $C_{1-20}$ hydrocarbyl groups, provided that one or both hydrocarbyl groups can form a cyclic structure with the carbon atom adjacent to Z, and each of $R^5$ and $R^6$, independently, is H, $C_{1-20}$ hydrocarbyl or a functional group selected from $-OR^2$, $-Cl$, $-CO_2R^2$, $-CO_2M$, $-C(O,N(R^1)_2$, $-C(O)R^2$, $-SR^2$, $-SO_2R^2$, $-OSO_2R^2$, $-SOR^2$, $-P(O)(OR^2)_{2-y}(R^1)_y$, $-CN$, $-NHR^2$, $-N(R^2)_2$,

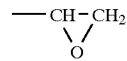

$-Si(OR^1)_{3-x}(R^1)_x$, $-OSi(OR^1)_{3-x}(R^1)_x$, $-NO_2$, $-SO_3M$, $-PO_3M_2$ and $-P(O)(OR^2)_2M$, wherein M is alkali or alkaline earth metal, ammonium, quaternary ammonium, phosphonium or arsonium, y is 0, 1 or 2, each $R^1$, independently, is H or $C_{1-20}$ hydrocarbyl, each $R^2$, independently, is $C_{1-20}$ hydrocarbyl, and x is 0 or an integer of 1 to 3, or $R^5$ and $R^6$, taken together with the carbon atoms to which they are attached, is a substituted or unsubstituted $C_{5-8}$ alicyclic, $C_{5-8}$ heterocyclic or $C_{4-14}$ aromatic ring, the heteroatom of the heterocyclic ring being selected from O, N and S. To illustrate the various structures when Z is a carbon atom, the grouping

may have the following structures

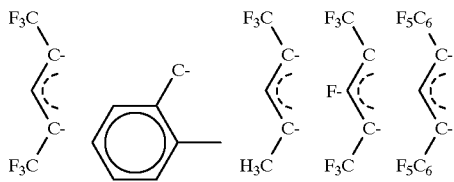

In defining the various groups present on the different formulas representing the catalysts, by hydrocarbyl is meant an aliphatic, alicyclic, aromatic or mixed aliphatic-aromatic monovalent radical, optionally containing one or more "polar substituents" and/or one or more in-chain heteroatoms which are inert under polymerizing conditions. Thus such hydrocarbyl groups may contain one or more straight chain or branched alkyl substituents having 1 to 12 carbons and more practically 1 to 6 carbons; or one or more halogen substituents, more practical of which are chlorine and fluorine; or one or more other type of substituents such as $-CN$, $-CO_2R^2$, $-R^2OR^2$, $-OR^2$, $-CON(R^2)_2$, and the like. The heterocyclic groups may also contain one or more of the above mentioned substituents. Illustrative examples of the hydrocarbyl groups are various simple straight chain and branched alkyl groups as well as the alkyl groups substituted with the above mentioned substituents which may be exemplified by chloroethyl group, fluoromethyl, perfluoroethyl, 6-fluorohexyl, pentafluorophenyl, tris(trifluoromethyl) phenyl and the like; furanyl, pyrrolyl, thiophenyl, dihydrofuranyl, pyrrolinyl, tetrahydrofuranyl, pyrrolidinyl, mono or dimethylpyrrolyl as well as such and similar heterocyclic groups which are substituted by the above mentioned substituents. It is important to remember that with regard to the various groups that may be present in the catalysts used in this invention, the exact length of a chain is not important, its specific configuration or the substituents that are present, provided that such substituents are unreactive under polymerizing conditions.

By "polar substituents" is meant polar radicals or groups which are unreactive under polymerizing conditions. Functional substituents include, but are not limited to, such groups as $-OH$, $OR^2$, $-Cl$, $-CO_2R^2$, $-CO_2M$, $-C(O)N(R^1)_2$, $-C(O)R^2$, $-SR^2$, $-SOR^2$, $-SO_2R^2$, $-OSO_2R^2$, $-P(O)(OR^2)_{2-y}(R^1)_y$, $-CN$, $-NHR^2$, $-N(R^2)_2$,

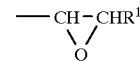

$-CF_3$, $-Si(OR^1)_{3-x}(R^1)_x$, $-OSi(OR^1)_{3-x}(R^1)_x$, $-NO_2$, $-SO_3M$, $-PO_3M_2$, $-P(O)(OR^2)_2M$, $-CO_2-Si(OR^1)_{3-x}(R^1)_x$ and $(R^1)_2Cr(CO)_5$ wherein M is alkali metal, ammonium or quaternary ammonium and $R^1$, $R^2$, x and y are as defined above.

The term "in-chain" (heteroatom) is intended to include both the main (backbone) chain and any side chain. Preferred in-chain heteroatoms are $-O-$, $-N-$ and $-S-$.

By weakly coordinating ligand ($L^1$) is meant a compound which can bond to nickel, but is readily displaced therefrom by the olefin which is being polymerized. Weakly coordinating ligands ($L^1$) include, but are not limited to pyridine, piperidine, dialkyl ethers, tetrahydrofuran, alkyl and aryl nitriles and dinitriles, alcohols, amides, aliphatic esters and tertiary amines. The chain length of the alkyl groups are not critical and usually will have 1 to 20 atoms and the aryl groups will usually have 6 to 14 carbon atoms.

By strongly coordinating ligand ($L^2$) is means a compound which can bond to nickel sufficiently strongly to displace therefrom part or all of the olefin which is being polymerized. Strongly coordinating ligands ($L^2$) include, but are not limited to, compounds of the formula $E^1(R^1)_3$ wherein $E^1$ and $R^1$ are as defined above.

By acceptor compound is meant a compound which reacts with or competitively bonds (complexes) with ligand $L^1$ or $L^2$. Acceptor compounds include, but are not limited to organic oxidants, such as amine oxides, peroxides, hydroperoxides, and alkylating compounds which oxidize the ligand rendering it less effective in complexing the catalytic metal. Such oxidants can be used effectively, for example, with phosphines which are oxidized to the corresponding phosphine oxides which are less effective complexants. Further acceptor compounds include and Group VIII metal complexes and Lewis acids. These compounds can bond reversibly or irreversibly with a ligand. Illustrative examples of oxidants include trimethylamine oxide, di-t-butylperoxide, cyclohexylhydroperoxide, methyl iodide, trimethylsilyl iodide and the like.

Illustrative examples of Group VIII metals and Lewis acids are bis(benzonitrile)-palladium dichloride, bis(1,5-cyclooctadiene)nickel(0), nickel tetracarbonyl, 2,4-pentanedionatobis(ethylene)rhodium(I), methylaluminumbis(2,6-di-tert-butyl-4-methylphenoxide) and ethylene pentacarbonylchromium(0).

By alkylating or arylating compound is meant a compound which is capable of chemically transferring alkyl and/or aryl groups, as the case may be, to nickel. Alkylating and arylating compounds include, but are not limited to, alkyl and aryl iodides, aluminum alkyls and aryls, transition metal alkyl- and aryl-containing compounds, such as dimethyl(1,5-cyclooctadiene)-platinum(II) and dimethylbis (phosphine)nickel, and other conventional reagents capable of transferring alkyl and/or aryl groups.

Additional nickel-containing compounds that may be used as catalysts in the method of this invention may be represented by the formula:

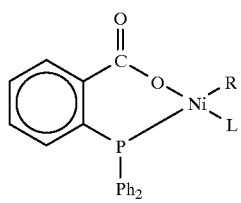

wherein L and R are as defined above, Ph is a phenyl group which may be unsubstituted or substituted with up to three alkyl groups having 1 to 8 carbon atoms. This class of compounds is disclosed in GB Patent 1,364,870 which is incorporated herein by reference.

Also useful compounds are nickel compounds containing chelating ligands bearing nitrogen and oxygen, such ligands being exemplified by 8-hydroxyquinoline, o-aminophenol and o-aminobenzoic acid, Illustrative examples of auxiliary ligand L are:

triphenylphosphine; triphenylphosphine methyleneylid; triphenylphosphite;
tris(2,4-di-t-butylphenyl)phosphite; pyridine; triphenylphosphine oxide; tris(o-tolyl)phosphine, and the like.

Referring to formula I, L can also be the "complex itself" in which X acts as the heteroatom, i.e., a dimer.

Illustrative examples of the nickel catalysts may be represented by the following formulas:

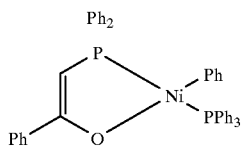

A

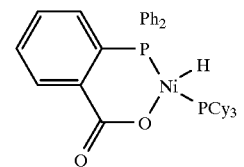

B

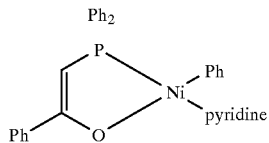

C

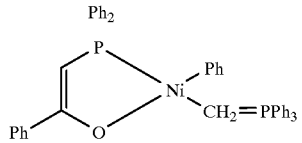

D

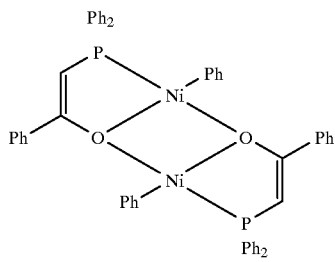

E

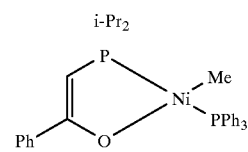

F

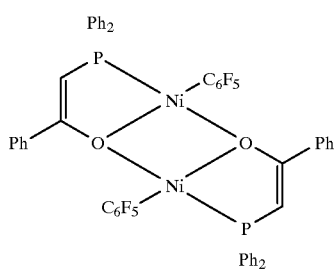

G

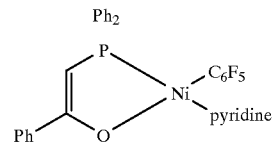

H

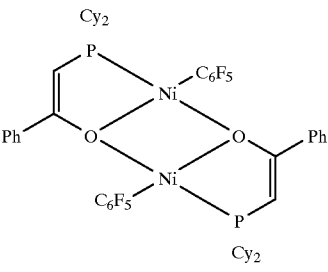

J

The catalysts of this invention can be conveniently prepared by methods well-documented in the literature. Alternatively the catalysts can be prepared in situ by reacting a suitable nickel compound with the desired ligand, optionally in the presence of a metal alkyl (e.g. triethylaluminum and the like) or a metal hydride (e.g. sodium borohydride and the like). A preferred method of generating an active catalyst in situ is to react bis(cyclooctadiene)nickel with an active hydrogen containing chelate ligand such as hexafluoroacetylacetone or (o-$C_6H_4$COOH)diphenylphosphine.

Catalysts G and J can be prepared by addition of chelating ligands containing phosphine and ketonic functionality to a stable bis(pentafluorophenyl)nickel complex, either the toluene, bis(tetrahydrofuran), or the bis(diethylether) complex. The intermediate bis(pentafluorophenyl)nickel chelate complex undergoes proton transfer (either inter- or intramolecular) from the chelate ligand to the pentafluorophenyl ligand thus forming pentafluorobenzene and the expected dimers G and J.

The nickel catalyst is suitably employed as an unsupported material. In certain modifications, the nickel catalyst can be supported on an inorganic, solid catalyst carrier which is normally solid under reaction conditions and is heterogeneous, i.e., is substantially insoluble in the reaction medium. Illustrative of suitable inorganic, solid catalyst carriers are inorganic acidic oxides such as alumina and inorganic materials known as refractory oxides. Suitable refractory oxides include synthetic components as well as acid treated clays and similar materials such as kieselguhr or crystalline macroreticular aluminosilicates known in the art as molecular sieves. In general, synthetic catalyst carriers are preferred over natural occurring materials or molecular sieves. Exemplary synthetic catalyst carriers include alumina, silica-alumina, silica-magnesia, silica-alumina-titania, silica-alumina-zirconia, silica-titania-zirconia, silica-magnesia-alumina, and the like. Particularly preferred catalyst carriers are siliceous refractory oxides containing up to 90% by weight of alumina, especially silica and silica-alumina.

When the catalyst composition is supported, the proportion of catalyst composition to carrier is not critical. In general, proportions of catalyst composition from 0.01% to 70% by weight, based on the catalyst carrier are satisfactory, with amounts of from 0.1% to 20% by weight, calculated on the same basis, being preferred. The catalyst composition is introduced onto the carrier in any suitable manner. In one modification, the supported catalyst composition is prepared by intimately contacting the preformed catalyst composition and the carrier in an inert diluent, preferably the same inert diluent employed for preparing the catalyst composition. In another modification, the catalyst composition can be prepared directly on the catalyst carrier support surface by contacting the catalyst composition precursors in the presence of the catalyst carrier in a suitable inert diluent.

The copolymers of the present invention are essentially amorphous and may be alternating or random, depending on the choice of catalyst and/or the ratio or the relative concentration of the monomers used. The monomers may be incorporated into the polymer in an amount of from about 1 mole % to about 80 mole % of at least one NB-type monomer, preferably from about 4 to about 65 mol percent and most preferably from about 40 to about 60 mole percent of the NB-type monomer. The corresponding balance of the monomer, to make up 100 percent, is ethylene. The amount of each comonomer may be selected depending on the desired properties of the resulting copolymer. For example, if a polymer having a higher glass transition temperature is desired, such as between 120° C. to 160° C., is desired, it is necessary to incorporate a higher mole percent amount of norbornene, such as between 40 and 60% Similarly, if a lower Tg polymer is desired, it is necessary to incorporate a lower mole percent of norbornene, such as between 20 and 30 mole percent to give Tg between 30 and 70° C. Different norbornene monomers give different behavior with regard to their effect on Tg. For example alkylnorbornenes all give lower Tg's than does norbornene itself at a given level of incorporation, with longer alkyl chains giving successively lower Tg's. On the other hand polycyclic norbornene-type monomers give higher Tg's than does norbornene for a given level of incorporation. For example tetracyclododecene gives a Tg in the range of 120 to 160° C. at only 25 to 35 mole % incorporation (compared to 40 to 60 mole % in the case of norbornene). Furthermore, it is possible to control the glass transition temperature by using a mixture of different NB-type monomers. More specifically, by replacing some norbornene with a substituted norbornene, such as alkyl norbornene, a lower Tg polymer results as compared to the copolymer if only norbornene were used.

Catalysts of formula I where E is phosphorus and X is oxygen have been found to preferably yield essentially alternating copolymers of norbornene and ethylene. Nevertheless at extremely high ratio of either one monomer over the other deviations from this alternating compositions are observed. When substituted norbornenes are employed, higher concentrations of the norbornenes are required to obtain the alternating compositions.

The polymerizations of this invention may be carried out in bulk or in a diluent. If the catalyst is soluble in the NB-type monomer being copolymerized, it may be convenient to carry out the polymerization in bulk. More often, however, it is preferable to carry out the copolymerization in a diluent. Any organic diluent or solvent which does not adversely interfere with the themlyst and is a solvent for the monomers may be employed. Examples of organic solvents are aliphatic (non-polar) hydrocarbons such as pentane, hexane, heptane, octane, decane and the like; alicyclic hydrocarbons such as cyclopentane and cyclohexane; aromatic hydrocarbons such as benzene, toluene, xylene and the like; halogenated (polar) hydrocarbons such as methylene chloride, ethyl chloride, 1,1-dichloroethane, 1,2-dichloroethane, 1,2-dichloroethylene, 1-chloropropane, 2-chloropropane, 1-chlorobutane, 2-chlorobutane, 1-chloro-2-methyl-propane, 1-chloropentane, chlorobenzene, o-dichlorobenzene, m-dichlorobenzene, p-dichlorobenzene. The preferred diluents are aliphatic and aromatic hydrocarbons such as isooctane, cyclohexane or toluene with the aromatic hydrocarbons being most preferred.

The instant method is unique in that it makes it possible to prepare copolymers of ethylene with NB-type monomers containing functional substituents such as esters, ethers or silyl groups as disclosed below in greater detail. The catalysts employed in the prior art in the polymerization of cyclic olefins were deactivated if such monomers contained functional substituents.

The copolymers may be prepared from 0 to 100 percent of functional NB-type type monomers or the NB-type monomers may contain 1 to 99 percent of non-functional and 1 to 99 percent of functional NB-type monomers. Practical categories of terpolymers are those containing 1 to 10 percent of functional NB-type monomers or those containing 20 to 50 percent of functional NB-type monomers. Another practical category are copolymers which contain 100 percent of one or more functional NB-type monomer(s). Due to the presence of functionality such copolymers possess exceptionally good adhesion and paintability properties.

As noted above, the copolymers of the present invention are essentially amorphous and include those that are substantially alternating as well as those that are largely random. Those copolymers which contain close to 50:50 mole ratio of each category of monomers will tend to be largely alternating. These copolymers are essentially amorphous in nature and exhibit glass transition temperatures in the range of approximately 0° C. to 200° C., preferably 80° C. to 180° C. and most preferably 100° C. to 150° C. The copolymers range in molecular weight (Mw) from about 1,000 to about 250,000, often from about 2,000 to about 150,000 and preferably from about 5,000 to about 125,000. Furthermore, essentially every copolymer chain is terminated with a vinyl end group originating from β-hydride elimination from the ultimate ethylene unit The copolymers prepared according to the method of this invention are generally amorphous, with low crystallinity. Consequently, they are transparent. Additionally, these copolymers have relatively low density, low birefringence and low water absorption. Furthermore, they have very desirable vapor barrier properties and good resistance to hydrolysis, acids and alkali and to weathering; very good electrical insulating properties, thermoplastic processing characteristics, high stiffness, modulus, hardness and melt flow. Accordingly, these copolymers may be used for optical storage media applications such as CD and CD-ROM, in optical uses such as lenses and lighting articles, in medical applications where gamma or steam sterilization is required, as films and in electronic and electrical applications.

NB-Type Monomers

This category of monomers are the NB-type monomers which are polycyclic and contain at least one norbornene-moiety and may be selected from those represented by the formula below:

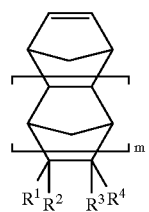

wherein $R^1$ to $R^4$ independently represents hydrogen, linear or branched ($C_1$ to $C_{10}$) alkyl, aromatic or saturated or unsaturated cyclic groups; a functional substituent selected from the group —$(CH_2)_n$—C(O)OR, —$(CH_2)_n$—OR, —$(CH_2)_n$—OC(O)R, —$(CH_2)_n$—C(O)R and —$(CH_2)_n$—OC(O)OR, —$(CH_2)_nC(R)_2CH(R)(C(O)OR)$, —$(CH_2)_nC(R)_2CH(C(O)OR)_2$, wherein R represents hydrogen, or linear and branched ($C_1$ to $C_{10}$) alkyl; or a silyl substituent represented as follows:

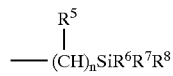

wherein $R^5$ independently represents hydrogen, methyl, or ethyl, $R^6$, $R^7$, and $R^8$ independently represent halogen selected from bromine, chlorine, fluorine, and iodine, linear or branched ($C_1$ to $C_{20}$) alkyl, linear or branched ($C_1$ to $C_{20}$) alkoxy, linear or branched ($C_1$ to $C_{20}$) alkyl carbonyloxy (e.g., acetoxy), linear or branched ($C_1$ to $C_{20}$) alkyl peroxy (e.g., t-butyl peroxy), substituted or unsubstituted ($C_6$ to $C_{20}$) aryloxy; any of $R^1$ and $R^2$ or $R^3$ and $R^4$ can be taken together to form a ($C_1$ to $C_{10}$) alkylidenyl group; m is an integer from 0 to 5; and n is an integer from 0 to 10, preferably n is 0. The silyl substituent could also be —$(CH_2)_n$—O—$SiR^6R^7R^8$ where n and the R groups are as defined above. $R^1$ and $R^4$ taken together with the two ring carbon atoms to which they are attached represent a saturated cyclic group of 4 to 8 carbon atoms, The cyclic group formed by $R^1$ and $R^4$ can be substituted by at least one of $R^2$ and $R^3$, the definition of which is set forth above. The NB-type monomers which contain one or more functional substituents are referred to as functional NB-type monomers.

As discussed above substituents $R^1$ and $R^4$ together with the two ring carbon atoms to which they are attached can form a saturated cyclic group of 4 to 8 carbon atoms. Generically such monomers are represented by the following structure:

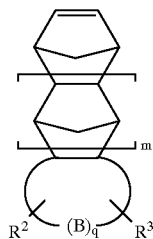

wherein B is a —$CH_2$— group and q is a number from 2 to 6. It should be apparent that when the carbon atom in the —$CH_2$— group represented by B is substituted by $R^2$ or $R^3$ (i.e., $R^2$ and $R^3$ are other than hydrogen), the —$CH_2$— group will have one less hydrogen atom attached thereto.

Representative structures are shown below:

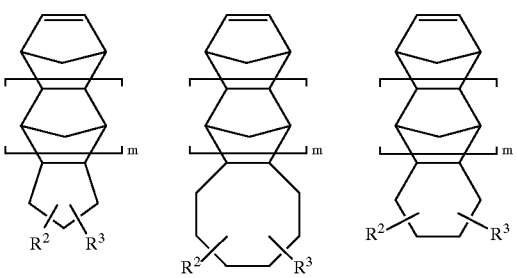

Polycyclic monomers of the above formula with a substituent selected from the group —$(CH_2)_nC(R)_2CH(R)(C(O)OR)$ or —$(CH_2)_nC(R)_2CH(C(O)OR)_2$ can be represented as follows:

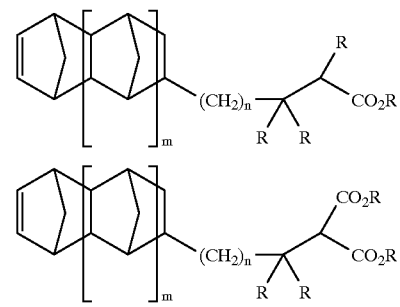

In the above formulae m is preferably 0 or 1, more preferably m is 0. When m is 0 the preferred structure is represented as follows:

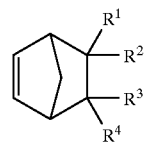

wherein $R^1$ to $R^4$ are previously defined.

Illustrative examples of suitable monomers include 2-norbornene, 5-butyl-2-norbornene, 5-methyl-2-norbornene, 5-hexyl-2-norbornene, 5-decyl-2-norbornene, 5-phenyl-2-norbornene, 5-naphthyl-2-norbornene 5-ethylidene-2-norbornene, vinylnorbornene, dicyclopentadiene, dihydrodicyclopentadiene, tetracyclododecene, methyltetracyclododecene, tetracyclododecadiene, dimethyltetracyclododecene, ethyltetracyclododecene, ethylidenyl tetracyclododecene, phenyltetracyclododecene, trimers of cyclopentadiene (e.g., symmetrical and asymmetrical trimers), 5-hydroxy-2-norbornene, 5-hydroxymethyl-2-norbornene, 5-methoxy-2-norbornene, 5-t-butoxycarbonyl-2-norbornene, 5-methoxycarbonyl-2-norbornene, 5-carboxy-2-norbornene, 5-carboxymethyl-2-norbornene, decanoic acid ester of 5-norbornene-2-methanol, octanoic acid ester of 5-norbornene-2-methanol, n-butyric acid ester of 5-norbornene-2-methanol, 5-triethoxysilyl-norbornene, 5-trichlorosilyl-norbornene, 5-trimethylsilyl norbornene, 5-chlorodimethylsilyl norbornene, 5-trimethoxysilyl norbornene, 5-methyldimethoxysilyl norbornene, and 5-dimethylmethoxy norbornene.

EXAMPLES

Preparation of Catalysts

Synthesis of Catalyst A. $Ni(PhC(O)CHPPh_2)(Ph)(PPh_3)$

This preparation followed a published report in *J. Polym. Sci.* 1987, 25, 1989. A toluene slurry (150 mL) of $PPh_3$ (5.00 g, 19.1 mmol) and the ylid $PhC(O)CHPPh_3$ (7.30 g, 19.1 mmol) was added to a chilled (0° C.) toluene slurry (80 mL) of $Ni(COD)_2$ (5.30 g, 19.1 mmol). Upon completion of the addition, the mixture became a red-brown slurry. The mixture was allowed to warm to room temperature and stirred for 21 hr. The mixture was then heated to 50° C. for 2 hr. The mixture was cooled to room temperature and allowed to stir for an additional 16 hr. The mixture was filtered to give a red-brown filtrate which upon removal of solvent in vacuo gave a brown residue. The residue was dissolved in toluene (50 mL) from which a tan precipitate formed upon addition of 50 mL of hexane. The mixture was stored in the freezer overnight to give a gold-tan solid which was filtered, washed with hexane, and dried. Yield 10.5 g (79%).

Synthesis of Catalyst B. $Ni(OC(O)(C_6H_4)PPh_2)(H)(PCy_3)$ $Ni(COD)_2$ (2.00 g, 7.27 mmol) was dissolved in 100 mL of toluene and cooled to –30° C. To this solution was added a toluene solution (50 mL) of 2-(diphenylphosphino)benzoic acid (2.22 g, 7.27 mmol). The mixture was stirred at –30° C. for 30 min and then warmed to –10° C. and stirred for one hour. To this mixture was added triphenylphosphine (2.03 g, 7.27 mmol) in 50 mL of toluene. The mixture was stirred at room temperature for one hour. The solvent was removed in vacuo to give a light yellow-brown solid. Yield of crude product was 2.87 g (61%).

Synthesis of Catalyst C

This catalyst was synthesized using a procedure published previously in *J. Polym. Sci.* 1987, 25, 1989.

Synthesis of Catalyst D

This catalyst was synthesized using a procedure published previously in *Angew. Chem., Int. Ed. Engl.* 1985, 24, 599.

Synthesis of Catalyst E

This catalyst was synthesized by reacting catalyst I (0.76 g) with $Rh(acetylacetonate)(C_2H_4)_2$ (0.14 g) in a minimum amount of toluene (about 25 mL). After stirring the mixture for 4 hours, the precipitated solid was filtered and dried overnight in vacuo to yield 0.48 g of a yellow-brown solid.

Synthesis of Catalyst F $Ni(PhC(O)CHP(I—Pr)_2)(Cl)(PPh_3)$ (0.50 g, 0.85 mmol) was dissolved in about 50 mL of dry, deoxygenated ether and cooled to –78° C. To this red-brown slurry was added MeLi (0.53 mL of a 1.4 M solution in ether). The mixture was allowed to warm to room temperature. The slurry became orange-brown. The mixture was stirred for several hours, then the solvent was removed in vacuo overnight. The resulting residue was dissolved in 20 mL of dry, deoxygenated toluene and filtered. The solvent was removed in vacuo from the filtrate to give a red-brown sticky solid.

Synthesis of Catalyst G $(\eta^6\text{-toluene})Ni(C_6F_5)_2$ (0.10 g, 0.21 mmol) was dissolved in 10 mL of toluene. To this solution $PPh_2CH_2C(O)Ph$ (0.063 g, 0.21 mmol) in 10 mL of toluene was added dropwise. The color of the solution turned yellow-brown after 10 m, and a yellow powder began to precipitate from solution. After stirring at room temperature for 1 h, the solvent was removed in vacuo resulting in a yellow solid. This was dissolved in 10 mL of $CH_2Cl_2$, filtered and stored at –20° C. Bright yellow crystals of $(PPh_2CH_2C(O)Ph)Ni(C_6F_5)_2$ were obtained in quantitative yield after 2 days.

Compound $(PPh_2CH_2C(O)Ph)Ni(C_6F_5)_2$ (0.39 g, 0.56 mmol) was dissolved in approximately 50 mL of 1,2-dichloroethane. The yellow solution was refluxed for 42 h during which time an orange color developed. Cooling the solution to room temperature resulted in an orange powder. The solvent was removed in vacuo to give an orange solid. Yield 0.28 g (93%).

Synthesis of Catalyst H

Pyridine (5 mL) was added to a toluene slurry of Catalyst VII (0.2 g) and stirred for 15 min. The volatiles were then removed in vacuo to yield a yellow powder.

Synthesis of Catalyst I $(\eta^6\text{-toluene})Ni(C_6F_5)_2$ (1.0 g, 2.0 mmol) was dissolved in 20 mL of 1,2-dichloroethane. To this solution $PCy_2CH_2C(O)Ph$ (0.63 g, 2.0 mmol) in 20 mL of 1,2-dichloroethane was added. The solution was stirred for 15 min and the volatiles were removed in vacuo. The oily solid was redissolved in 1,2-dichloroethane (25 mL) and warmed to 65° C. overnight. The resulting solution was cooled to room temperature and then to –20° C. overnight. Orange crystals were collected by filtration and dried. Yield 0.65 g.

Synthesis of methyl aluminum bis(2,6-di-tert-butyl-4-methylphenoxide)

This material was prepared as described in *Macromolecules* 1994, 27, 2820.

Polymerizations

Polymerization Example 1

To a clean, dry 500 mL stainless steel reactor 40.0 g (425 mmol) of norbornene in 150 mL of dry, deoxygenated toluene was added under nitrogen, followed by triethoxysilyl norbornene (5.0 ml, 19.1 mmol). The reactor temperature was allowed to remain at ambient temperature and the stirred solution was saturated with ethylene. Catalyst C (0.11 g, 0.212 mmol) in a minimum amount of toluene was then added to the reactor. The reactor was then pressurized to 350 psig with ethylene. The reaction was allowed to proceed 2 h at which time the ethylene pressure was vented, the reactor was lowered and the solution was added to an excess of methanol. The terpolymer product precipitated from solution and was filtered and washed with excess methanol. After drying to constant weight (overnight in a vacuum oven at ambient temperature) the yield of terpolymer amounted to 24.0 grams. GPC showed the terpolymer to have an Mw of 41,500 and an Mn of 18,600. NMR revealed the composition to be ethylene, 57.6 mole percent, norbornene, 40.6 mole percent and triethoxysilyl norbornene, 1.8% mol.

Polymerization Example 2

To a clean, dry 500 mL stainless steel reactor 20.0 g of 5-butylnorbornene (133 mmol) in 150 mL of dry, deoxygenated toluene was added under nitrogen. The reactor temperature was allowed to remain at ambient temperature, and was saturated with ethylene. To the reactor was added catalyst C (0.0346 g, 0.067 mmol) in toluene (5 mL). The reactor was then pressurized to 300 psig with ethylene. The reaction was allowed to proceed 2 h at which time the ethylene pressure was vented, the reactor was lowered and the solution was poured into an excess of MeOH to precipitate the polymer which was subsequently filtered and dried in a vacuum oven (at 80° C.) overnight. Yield 10.5 g. $M_w$=65,520 and $M_n$=29,520. NMR spectroscopy confirmed the product to be a copolymer of ethylene and butylnorbornene.

Polymerization Example 3

To a clean, dry 500 mL stainless steel reactor 16.0 g of norbornene and 10.9 g of 5-triethoxysilylnorbornene in 150 mL of dry, deoxygenated toluene were added under nitrogen. The reactor temperature was allowed to remain at ambient temperature. To the reactor was added catalyst D (0.076 g, 0.11 mmol) in a minimum amount of toluene. The reactor was then pressurized to 100 psig with ethylene. The reaction was allowed to proceed 2 h at which time the ethylene pressure was vented, the reactor was lowered and the solution was poured into an excess of acetone to precipitate the polymer which was subsequently filtered and dried in a vacuum oven overnight. Yield 0.81 g. $M_w$=19,600 and $M_n$=9,930. The incorporation of ethylene was determined to be 55 mole percent and the incorporation of 5-triethoxysilylnorbornene was determined to be 10 mole percent by NMR spectroscopy.

Polymerization Example 4

To a clean, dry 500 mL stainless steel reactor 20.0 g of norbornene in 150 mL of dry, deoxygenated toluene was added under nitrogen. The reactor temperature was allowed to remain at ambient temperature. To the reactor was added catalyst D (0.075 g, 0.11 mmol) in a minimum amount of toluene. The reactor was then pressurized to 50 psig with ethylene. The reaction was allowed to proceed 2 h at which time the ethylene pressure was vented, the reactor was lowered and the solution was poured into an excess of MeOH to precipitate the polymer which was subsequently filtered and dried in a vacuum oven overnight. Yield 1.5 g. $M_w$=32,500 and $M_n$=14,300. The incorporation of ethylene was determined to be 51 mole percent by NMR spectroscopy. Glass transition temperature was determined to be 123° C. by DSC.

Polymerzation Example 5

To a clean, dry 500 mL stainless steel reactor 20.0 g of norbornene in 150 mL of dry, deoxygenated toluene was added under nitrogen. The reactor temperature was allowed to remain at ambient temperature. To the reactor was added catalyst A (0.074 g, 0.11 mmol) in a minimum amount of toluene. The reactor was then pressurized to 100 psig with ethylene. The reaction was allowed to proceed 2 h at which time the ethylene pressure was vented, the reactor was lowered and the solution was poured into an excess of MeOH. The solvent was allowed to evaporate overnight. Yield 7.0 g. $M_w$=2,500 and $M_n$=1,400. The incorporation of ethylene was determined to be 46 mole percent by NMR spectroscopy.

Polymerization Example 6

To a clean, dry 500 mL stainless steel reactor 20.0 g of norbornene in 150 mL of dry, deoxygenated toluene was added under nitrogen. The reactor was warmed to 50° C. To the reactor was added a solution of Ni(COD)$_2$ (0.029 g, 0.11 mmol) and PPh$_3$=CHC(O)Ph (0.041 g, 0.11 mmol) in a minimum amount of toluene. The reactor was then pressurized to 100 psig with ethylene. The reaction was allowed to proceed 2 h at which time the ethylene pressure was vented, the reactor was lowered and the solution was poured into an excess of MeOH and was allowed to evaporate. Yield 2.0 g. $M_w$=34,700 and $M_n$=14,800. The incorporation of ethylene was determined to be 51 mole percent by NMR spectroscopy. Glass transition temperature was determined to be 111° C. by DSC.

Polymerization Example 7

To a clean, dry 500 mL stainless steel reactor 20.0 g of norbornene in 150 mL of dry, deoxygenated toluene was added under nitrogen. The reactor was allowed to remain at ambient temperature. To the reactor was added a solution of Ni(COD)$_2$ (0.029 g, 0.11 mmol) and PPh$_3$=CHC(O)Ph (0.041 g, 0.11 mmol) in a minimum amount of toluene. The reactor was then pressurized to 100 psig with ethylene. The reaction was allowed to proceed 2 h at which time the ethylene pressure was vented, the reactor was lowered and the solution was poured into an excess of MeOH to precipitate the polymer which was subsequently filtered and dried in a vacuum oven overnight. Additional polymer was isolated from the filtrate after evaporation of the solvents. Yield 1.3 g. $M_w$=60,000 and $M_n$=27,500. The incorporation of ethylene was determined to be 54 mole percent by NMR spectroscopy. Glass transition temperature was determined to be 110° C. by DSC.

Polymerization Example 8

To a clean, dry 500 mL stainless steel reactor 20.0 g of norbornene in 150 mL of dry, deoxygenated toluene was added under nitrogen. The reactor was allowed to remain at ambient temperature. To the reactor was added a solution of catalyst E (0.047 g, 0.053 mmol) in a minimum amount of toluene. The reactor was then pressurized to 100 psig with ethylene. The reaction was allowed to proceed 2 h at which time the ethylene pressure was vented, the reactor was lowered and the solution was poured into an excess of MeOH to precipitate the polymer. The polymer was filtered and dried in a vacuum oven overnight. Yield 10.1 g. $M_w$=59,600 and $M_n$=28,900. The incorporation of ethylene was determined to be 55 mole percent by NMR spectroscopy.

Polymerization Example 9

To a clean, dry 500 mL stainless steel reactor 20.0 g of norbornene in 150 mL of dry, deoxygenated toluene was added under nitrogen. The reactor was allowed to remain at ambient temperature. To the reactor was added a solution of catalyst D (0.075 g, 0.105 mmol) in a minimum amount of toluene. The reactor was then pressurized to 100 psig with ethylene. The reaction was allowed to proceed 2 h at which time the ethylene pressure was vented, the reactor was lowered and the solution was poured into an excess of MeOH to precipitate the polymer. The polymer was filtered and dried in a vacuum oven overnight. Yield 2.1 g. $M_w$=44,300 and $M_n$=28,900. The incorporation of ethylene was determined to be 59 mole percent by NMR spectroscopy.

Polymerization Example 10

To a clean, dry 500 mL stainless steel reactor 20.0 g of norbornene in 150 mL of dry, deoxygenated toluene was added under nitrogen. The reactor was allowed to remain at ambient temperature. To the reactor was added a solution of catalyst C (0.054 g, 0.11 mmol) in a minimum amount of toluene. The reactor was then pressurized to 100 psig with ethylene. The reaction was allowed to proceed 2 h at which time the ethylene pressure was vented, the reactor was lowered and the solution was poured into an excess of MeOH to precipitate the polymer. The polymer was filtered and dried in a vacuum oven overnight. Yield 8.43 g. $M_w$=75,900 and $M_n$=37,200. The incorporation of ethylene was determined to be 57 mole percent by NMR spectroscopy. Glass transition temperature was determined to be 106° C. by DSC.

Polymerization Example 11

To a clean, dry 500 mL stainless steel reactor 20.0 g of norbornene in 150 mL of dry, deoxygenated toluene was added under nitrogen. The reactor was allowed to remain at ambient temperature. To the reactor was added a solution of catalyst E (0.047 g, 0.053 mmol) and methylaluminum bis(2,6-di-tert-butyl-4-methylphenoxide) (0.051 g, 0.11 mmol) in a minimum amount of toluene. The reactor was then pressurized to 100 psig with ethylene. The reaction was allowed to proceed 2 h at which time the ethylene pressure was vented, the reactor was lowered and the solution was poured into an excess of MeOH to precipitate the polymer. The polymer was filtered and dried in a vacuum oven overnight. Additional polymer was retrieved from the filtrate after evaporation of solvent. Yield 7.4 g. $M_w$=81,500 and $M_n$=34,800. The incorpoation of ethylene was determined to be 58 mole percent by NMR spectroscopy.

Polymerization Example 12

To a clean, dry 500 mL stainless steel reactor 20.0 g of norbornene in 150 ml of dry, deoxygenated toluene was added under nitrogen. The reactor was allowed to remain at ambient temperature. To the reactor was added a solution of catalyst C (0.054 g, 0.11 mmol) and methylaluminum bis (2,6-di-tert-butyl-4-methylphenoxide) (0.051 g, 0.11 mmol) in a minimum amount of toluene. The reactor was then pressurized to 100 psig with ethylene. The reaction was allowed to proceed 2 h at which time the ethylene pressure was vented, the reactor was lowered and the solution was poured into an excess of MeOH to precipitate the polymer. The solid was redissolved in toluene and reprecipitated from MeOH. The polymer was filtered and dried in a vacuum oven overnight. Additional polymer was retrieved from the filtrate after evaporation of solvent. Yield 12.7 g. $M_w$=74,600 and $M_n$=38,900. The incorporation of ethylene was determined to be 57 mole percent by NMR spectroscopy.

Polymerization Example 13

To a clean, dry 500 mL stainless steel reactor 20.0 g of norbornene in 150 mL of dry, deoxygenated toluene was added under nitrogen. The reactor was allowed to remain at ambient temperature. To the reactor was added a solution of catalyst E (0.047 g, 0.053 mmol) and methylaluminum bis(2,6di-tert-butyl-4-methylphenoxide) (0.26 g, 0.53 mmol) in a minimum amount of toluene. The reactor was then pressurized to 100 psig with ethylene. The reaction was allowed to proceed 2 h at which time the ethylene pressure was vented, the reactor was lowered and the solution was poured into an excess of MeOH to precipitate the polymer. The polymer was filtered and dried in a vacuum oven overnight. Yield 0.32 g. $M_w$=52,900 and $M_n$=25,000. The incorporation of ethylene was determined to be 56 mole percent by NMR spectroscopy.

Polymerization Example 14

To a clean, dry 500 mL stainless steel reactor 40.0 g of norbornene in 150 mL of dry, deoxygenated toluene was added under nitrogen. The reactor was allowed to remain at ambient temperature. To the reactor was added a solution of catalyst E (0.047 g, 0.053 mmol) and methylaluminum bis(2,6-di-tert-butyl-4-methylphenoxide) (0.047 g, 0.11 mmol) in a minimum amount of toluene. The reactor was then pressurized to 50 psig with ethylene. The reaction was allowed to proceed 2 h at which time the ethylene pressure was vented, the reactor was lowered and the solution was poured into an excess of MeOH to precipitate the polymer. The polymer was filtered and dried in a vacuum oven overnight. Additional polymer was retrieved from the filtrate after evaporation of solvent. Yield 1.0 g. $M_w$=89,000 and $M_n$=28,100. The incorporation of ethylene was determined to be 42 mole percent by NMR spectroscopy. Glass transition temperature was determined to be 140° C. by DSC.

Polymerization Example 15

To a clean, dry 500 mL stainless steel reactor 20.0 g of norbornene in 150 mL of dry, deoxygenated toluene was added under nitrogen. The reactor was allowed to remain at ambient temperature. To the reactor was added a solution of catalyst E (0.047 g, 0.053 mmol) and triethylaluminum (0.11 mL of a 1 M solution in cyclohexane) in a minimum amount of toluene. The reactor was then pressurized to 100 psig with ethylene. The reaction was allowed to proceed 2 h at which time the ethylene pressure was vented, the reactor was lowered and the solution was poured into an excess of MeOH to precipitate the polymer. The polymer was filtered and dried in a vacuum oven overnight. Yield 5.2 g. $M_w$=67,700 and $M_n$=33,000. The incorporation of ethylene was determined to be 42 mole percent by NMR spectroscopy. The elongation of this copolymer was determined to be 7%.

Polymerization Example 16

To a clean, dry 500 mL stainless steel reactor 40.0 g of norbornene in 150 mL of dry, deoxygenated toluene was added under nitrogen. The reactor was allowed to remain at ambient temperature. To the reactor was added a solution of catalyst C (0.055 g, 0.11 mmol) and triethylaluminum (0.048 g of a 25 wt % solution in cyclohexane, 0.11 mmol) in a minimum amount of toluene. The reactor was then pressurized to 50 psig with ethylene. The reaction was allowed to proceed 2 h at which time the ethylene pressure was vented, the reactor was lowered and the solution was allowed to evaporate. Yield 0.8 g. $M_w$=41,800 and $M_n$=17,600. The incorporation of ethylene was determined to be 53 mole percent by NMR spectroscopy.

Polymerization Example 17

To a clean, dry 500 mL stainless steel reactor 20.0 g of norbornene in 150 mL of dry, deoxygenated toluene was added under nitrogen. The reactor was allowed to remain at ambient temperature. To the reactor was added a solution of catalyst C (0.054 g, 0.11 mmol) and methylaluminum bis (2,6-di-tert-butyl-4-methylphenoxide) (0.26 g, 0.53 mmol) in a minimum amount of toluene. The reactor was then pressurized to 100 psig with ethylene. The reaction was allowed to proceed 2 h at which time the ethylene pressure was vented, the reactor was lowered and the solution was poured into an excess of MeOH. The mixture was allowed to evaporate. Yield 1.4 g. $M_w$=46,300 and $M_n$=7,900.

Polymenzation Example 18

To a clean, dry 500 mL stainless steel reactor 20.0 g of norbornene in 150 mL of dry, deoxygenated toluene was added under nitrogen. The reactor was allowed to remain at ambient temperature. To the reactor was added a solution of catalyst E (0.047 g, 0.053 mmol) and triethylaluminum (0.55 mL of a 1 M solution in cyclohexane) in a minimum amount of toluene. The reactor was then pressurized to 100 psig with ethylene. The reaction was allowed to proceed 2 h at which time the ethylene pressure was vented, the reactor was lowered and the solution was poured into an excess of MeOH to precipitate the polymer. The mixture was allowed to evaporate. Yield 0.22 g.

Polymerization Example 19

To a clean, dry 500 mL stainless steel reactor 34.0 g of norbornene in 200 mL of dry, deoxygenated isooctane was added under nitrogen. The reactor was warmed to 60° C. To the reactor was added catalyst A (0.25 g) in a minimum amount of toluene. The reactor was then pressurized to 200 psig with ethylene. The reaction was allowed to proceed 1 h at which time the ethylene pressure was vented, the reactor was cooled, lowered and the solution was poured into an excess of MeOH. Oily droplets resulted. The solvent was allowed to evaporate to give a sticky solid. Yield 12.0 g. $M_w$=960 and $M_n$=840.

Polymerization Example 20

To a clean, dry 500 mL stainless steel reactor 20.0 g of norbornene in 150 mL of dry, deoxygenated toluene was added under nitrogen. The reactor was warmed to 60° C. To the reactor was added catalyst G (0.049 g, 0.049 mmol) in a minimum amount of toluene. The reactor was then pressurized to 200 psig with ethylene. The reaction was allowed to proceed 3 h at which time the ethylene pressure was vented, the reactor was lowered and the solution was poured into an excess of MeOH. The solvent was allowed to evaporate. Yield 0.1 g. The incorporation of ethylene was determined to be 58 mole percent by NMR spectroscopy.

Polymerization Example 21

To a clean, dry 500 mL stainless steel reactor 10.0 g of norbornene in 150 mL of dry, deoxygenated toluene was added under nitrogen. The reactor temperature was allowed to remain at ambient temperature. To the reactor was added catalyst F (0.035 g) in a minimum amount of toluene. The reactor was then pressurized to 100 psig with ethylene. The reaction was allowed to proceed 2 h at which time the ethylene pressure was vented, the reactor was lowered and the solution was allowed to evaporate overnight. Yield 0.1 g.

Polymerization Example 22

To a clean, dry 500 mL stainless steel reactor 20.0 g of norbornene in 150 mL of dry, deoxygenated toluene was added under nitrogen. The reactor was allowed to remain at ambient temperature. To the reactor was added a solution of catalyst C (0.054 g, 0.11 mmol) and methylaluminum bis (2,6-di-tert-butyl-4-methylphenoxide) (0.051 g, 0.11 mmol) in a minimum amount of toluene. The reactor was then pressurized to 100 psig with ethylene. The reaction was allowed to proceed 2 h at which time the ethylene pressure was vented, the reactor was lowered and the solution was poured into an excess of MeOH to precipitate the polymer. The polymer was filtered and dried in a vacuum oven overnight. Yield 5.3 g. $M_w$=64,000 and $M_n$=26,000. The incorporation of ethylene was determined to be 59 mole percent and the incorporation of the 5-methylester-2-norbornene was determined to be 2 mole percent by NMR spectroscopy. Glass transition temperature was determined to be 115° C. by DSC. The elongation of this copolymer was determined to be 8–9%.

Polymerization Example 23

To a clean, dry 500 mL stainless steel reactor 20.0 g of norbornene in 150 mL of dry, deoxygenated toluene was added under nitrogen. The reactor temperature was allowed to remain at ambient temperature. Catalyst F (0.061 g) and Ni(COD)$_2$ (0.030 g) in a minimum amount of toluene were mixed and then added to the reactor. The reactor was then pressurized to 100 psig with ethylene. The reaction was allowed to proceed 2 h at which time the ethylene pressure was vented, the reactor was lowered and the solution was added to an excess of MeOH and then allowed to evaporate overnight. Yield 2.2 g.

Polymerization Example 24

To a clean, dry 500 mL stainless steel reactor 36.0 g (383 mmol) of norbornene in 150 mL of dry, deoxygenated toluene was added under nitrogen, followed by triethoxysilylnbrbornene (11.1 ml, 43 mmol). The reactor temperature was allowed to remain at ambient temperature and the stirred solution was saturated with ethylene. Catalyst C (0.11 g, 0.212 mmol) in a minimum amount of toluene was then added to the reactor. The reactor was then pressurized to 100 psig with ethylene. The reaction was allowed to proceed 4 h at which time the ethylene pressure was vented, the reactor was lowered and the solution was added to an excess of MeOH. The terpolymer product precipitated from solution and was filtered and washed with excess methanol. After drying to constant weight (overnight in a vacuum oven at ambient temperature) the yield of terpolymer amounted to 5.0 grams. Proton NMR showed the terpolymer to comprise 52 mole percent ethylene, 44 mole percent norbornene and 4 mole percent triethoxysilylnorbornene.

Polymerization Example 25

To a clean, dry 500 mL stainless steel reactor 5 ml (19.1 mmol) of triethoxysilylnorbornene in 150 mL of dry, deoxygenated toluene was added under nitrogen. The reactor temperature was allowed to remain at ambient temperature and the stirred solution was saturated with ethylene. Catalyst C (0.11 g, 0.212 mmol) in a minimum amount of toluene was then added to the reactor. The reactor was then pressurized to 350 psig with ethylene. The reaction was allowed to proceed 2 h at which time the ethylene pressure was vented, the reactor was lowered and the solution was added to an excess of MeOH. The copolymer product precipitated from solution and was filtered and washed with excess methanol. After drying to constant weight (overnight in a vacuum oven at ambient temperature) the yield of copolymer amounted to 4.5 grams. Proton NMR showed the copolymer to comprise 95 mole percent ethylene and 5 mole percent triethoxysilylnorbornene. GPC showed the copolymer to have an Mw of 18,900 and an Mn of 9,100.

Polymerization Example 26

To a clean, dry 500 mL stainless steel reactor 5-triethoxysilyl-norbornene (50 mL, 191 mmol) in 100 mL of dry, deoxygenated toluene was added under nitrogen. The reactor temperature was allowed to remain at ambient temperature, and was saturated with ethylene. To the reactor was added catalyst C (0.11 g, 0.212 mmol) in toluene (7 mL). The reactor was then pressurized to 385 psig with ethylene. The reaction was allowed to proceed 2 h at which time the ethylene pressure was vented, the reactor was lowered and the solution was poured into an excess of MeOH to precipitate the polymer which was subsequently filtered and dried in a vacuum oven (at 25° C.) overnight. Yield 12.3 g. NMR spectroscopy confirmed the product to be a copolymer of ethylene and triethoxysilylnorbornene.

Polymerization Example 27

To a clean, dry 500 mL stainless steel reactor 50 mL (191 mmol) of triethoxysilylnorbornene in dry, deoxygenated toluene (150 mL total volume) was added under nitrogen. The reactor temperature was allowed to remain at ambient temperature and the stirred solution was saturated with ethylene. Catalyst C (0.11 g, 0.212 mmol) in a minimum amount of toluene was then added to the reactor. The reactor was then pressurized to 380 psig with ethylene and the ethylene tank was closed after the system had equilibrated. The reaction was allowed to proceed 2 h at which time the ethylene pressure (which had dropped to about 340 psi) was vented, the reactor was lowered and the solution was added to an excess of MeOH. The copolymer product precipitated from solution and was filtered and washed with excess methanol. After drying to constant weight (overnight in a vacuum oven at ambient temperature) the yield of copolymer amounted to 12.3 grams.

Polymerization Example 28

To a clean, dry 500 mL stainless steel reactor 18.05 g (192 mmol) of norbornene in 150 mL of dry, deoxygenated toluene was added under nitrogen, followed by 5-norbornene-2-yl acetate (3.238 g, 21.3 mmol) in toluene (10 mL). The reactor temperature was allowed to remain at ambient temperature and the stirred solution was saturated with ethylene. Catalyst C (0.0535 g, 0.106 mmol) in a minimum amount of toluene was then added to the reactor. The reactor was then pressurized to 300 psig with ethylene. The reaction was allowed to proceed 2 h at which time the ethylene pressure was vented, the reactor was lowered and the solution was added to an excess of MeOH. The terpolymer product precipitated from solution and was filtered and washed with excess methanol. After drying to constant weight (overnight in a vacuum oven at ambient temperature) the yield of terpolymer amounted to 1.41 grams. Proton NMR confirmed the incorporation of all three monomers and the GPC data revealed the Mw to be 21,580 and the Mn 11,270.

Polymerization Example 29

To a clean, dry 500 mL stainless steel reactor 18.05 g (192 mmol) of norbornene in 150 mL of dry, deoxygenated toluene was added under nitrogen, followed by the l-butyl ester of norbornene-5-carboxylic acid (4.132 g, 21.3 mmol) in toluene (10 mL). The reactor temperature was allowed to remain at ambient temperature and the stirred solution was saturated with ethylene. Catalyst C (0.0535 g, 0.106 mmol) in a minimum amount of toluene was then added to the reactor. The reactor was then pressurized to 300 psig with ethylene. The reaction was allowed to proceed 2 h at which time the ethylene pressure was vented, the reactor was lowered and the solution was added to an excess of MeOH. The terpolymer product precipitated from solution and was filtered and washed with excess methanol. After drying to constant weight (overnight in a vacuum oven at ambient temperature) the yield of terpolymer amounted to 5.53 grams. Proton NMR confirmed the incorporation of all three monomers and the GPC data revealed the Mw to be 40,770 and the Mn 21,430.

Polymerization Example 30

To a clean, dry 500 mL stainless steel reactor 18.05 g (192 mmol) of norbornene in 150 mL of dry, deoxygenated toluene was added under nitrogen, followed by triethoxysilylnorbornene (5.453 g, 21.3 mmol) in toluene (10 mL). The reactor temperature was allowed to remain at ambient temperature and the stirred solution was saturated with ethylene. Catalyst C (0.0535 g, 0.106 mmol) in a minimum amount of toluene was then added to the reactor. The reactor was then pressurized to 300 psig with ethylene. The reaction was allowed to proceed 2 h at which time the ethylene pressure was vented, the reactor was lowered and the solution was added to an excess of MEOH. The terpolymer product precipitated from solution and was filtered and washed with excess methanol. After drying to constant weight (overnight in a vacuum oven at ambient temperature) the yield of terpolymer amounted to 4.5 grams. Proton NMR confirmed the incorporation of all three monomers and the GPC data revealed the Mw to be 43,700 and the Mn 23,640.

Polymerization Example 31

To a clean, dry 500 mL stainless steel reactor 16.0 g (170 mmol) of norbornene and methylnorbornene (4.58 g, 4.25 mmol) in 150 mL of dry, deoxygenated toluene were added under nitrogen. The reactor temperature was allowed to remain at ambient temperature and the stirred solution was saturated with ethylene. Catalyst C (0.0535 g, 0.106 mmol) in a minimum amount of toluene was then added to the reactor. The reactor was then pressurized to 300 psig with ethylene. The reaction was allowed to proceed 2 h at which time the ethylene pressure was vented, the reactor was lowered and the solution was added to an excess of MeOH. The terpolymer product precipitated from solution and was filtered and washed with excess methanol. After drying to constant weight (overnight in a vacuum oven at 80° C.) the yield of glassy copolymer amounted to between 5 and 6 grams. Proton NMR confirmed the incorporation of all three monomers.

Polymerization Example 32

To a clean, dry 500 mL stainless steel reactor 18.05 g (192 mmol) of norbornene and the methylester of norbornene-5-carboxylic acid (3.24 g, 21.3 mmol) in 150 mL of dry, deoxygenated toluene were added under nitrogen. The reactor was allowed to remain at ambient temperature. To the reactor was added a solution of catalyst C (0.054 g, 0.1 mmol) and methylaluminum bis(2,6-di-tert-butyl-4-methylphenoxide) (0.047 g, 0.11 mmol) in a minimum amount of toluene. The reactor was then pressurized to 100 psig with ethylene. The reaction was allowed to proceed 2 h at which time the ethylene pressure was vented, the reactor was lowered and the solution was poured into an excess of MeOH to precipitate the polymer. The resulting terpolymer was filtered and dried in a vacuum oven overnight. Yield 5.3 g. $M_w$=64,000 and $M_n$=26,000. The incorporation of ethylene was determined to be 59 mole percent, norbornene 39 mole percent and the methyl ester 2 mole percent by NMR spectroscopy.

Polymerization Example 33

To a clean, dry 500 mL stainless steel reactor 40.0 g of norbornene in 150 mL of dry, deoxygenated toluene was added under nitrogen. The reactor temperature was allowed to remain at ambient temperature. To the reactor was added catalyst D (0.15 g, 0.21 mmol) in a minimum amount of toluene. The reactor was then pressurized to 100 psig with ethylene. The reaction was allowed to proceed 2 h at which time the ethylene pressure was vented, the reactor was lowered and the solution was poured into an excess of MeOH to precipitate the polymer which was subsequently filtered and dried in a vacuum oven overnight. Yield 9.1 g. $M_w$=30,000 and $M_n$=13,800. The incorporation of ethylene was determined to be 54 mole percent by NMR spectroscopy.

Polymerization Example 34

To a clean, dry 50 mL Schlenk flask, which was purged with argon gas was added [COD]$_2$Ni (0.16 g, 0.905 mmol), and dry, degassed toluene (9 mL). N-cyclohexylsalicylaldimine (0.183 g, 0.905 mmol) was placed in a 50 mL Wheaton serum bottle and dissolved in toluene (9 mL). This solution was added to the Schlenk flask dropwise over a 10 minute period. The solution was stirred at ambient temperature and pressure for 18 hours. A dark red solution containing a fine green precipitate of N-cyclohexylsalicylaldimine [COD] nickel was obtained.

To a clean, dry 500 mL stainless steel reactor was added (under nitrogen) norbornene (5 g) dissolved in toluene (total volume of the solution was 150 mL). The reactor was then flushed with ethylene and pressurized to 61 psi for 30 minutes in order to saturate the solution. The ethylene pressure was reduced to 15 psi and N-cyclohexylsalicylaldimine [COD] nickel (9.8 mg, 0.0265 mmol), prepared as described above, dissolved in toluene (0.5 mL), was added and the ethylene pressure was raised to 61 psi. The reaction was allowed to continue with vigorous stirring for 1 hour. The ethylene presssure was released, the reactor opened and the resulting solution was poured into 1.5 L of methanol, filtered and the resulting solid was dried overnight at 80° C. The yield of copolymer was 0.1 g and proton NMR revealed the composition to be approximately 49 mole percent norbornene and 51 mole percent ethylene.

Polymerization Example 35

To a clean, dry 500 mL stainless steel reactor 10.0 g (106.5 mmol) of norbornene and 5-butylnorbornene (15.975 g, 106.5 mmol) in 150 mL of dry, deoxygenated toluene were added under nitrogen. The reactor temperature was allowed to remain at ambient temperature and the stirred solution was saturated with ethylene. Catalyst C (0.11 g, 0.212 mmol) in a minimum amount of toluene was then added to the reactor. The reactor was then pressurized to 300 psig with ethylene. The reaction was allowed to proceed 2 h at which time the ethylene pressure was vented, the reactor was lowered and the solution was added to an excess of MeOH. The terpolymer product precipitated from solution and was filtered and washed with excess methanol. After drying to constant weight (overnight in a vacuum oven at 80° C.) the yield of terpolymer amounted to 23.3 grams. Proton NMR confirmed the incorporation of all three monomers and the GPC data revealed the Mw to be 39,000 and the Mn 19,350.

Polymerization Example 36

To a clean, dry 500 mL stainless steel reactor 16.0 g (170 mmol) of norbornene and 5-methylnorbornene (4.58 g, 42.5 mmol) in 150 mL of dry, deoxygenated toluene were added under nitrogen. The reactor temperature was allowed to remain at ambient temperature and the stirred solution was saturated with ethylene. Catalyst C (0.0535 g, 0.106 mmol) in a minimum amount of toluene was then added to the reactor. The reactor was then pressurized to 300 psig with ethylene. The reaction was allowed to proceed 2 h at which time the ethylene pressure was vented, the reactor was lowered and the solution was added to an excess of MEOH. The terpolymer product precipitated from solution and was filtered and washed with excess methanol. After drying to constant weight (overnight in a vacuum oven at 80° C.) the yield of terpolymner amounted to 17.8 grams. Proton NMR confirmed the incorporation of all three monomers and the GPC data revealed the Mw to be 13,100 and the Mn 7,900.

Polymerization Example 37

To a clean, dry 500 mL stainless steel reactor 40.0 g (425 mmol) of norbornene in 150 mL of dry, deoxygenated toluene was added under nitrogen. The reactor temperature was allowed to remain at ambient temperature and the stirred solution was saturated with ethylene. Bis(cycloctadiene)nickel(0) (0.244 g, 0.88 mmol) in toluene (4 mL) was then added to the reactor, followed by hexafluoroacetylacetone (0.14 mL, 1.0 mmol). The reactor was then pressurized to 250 psig with ethylene. The reaction was allowed to proceed 1 h at which time the ethylene pressure was vented, the reactor was lowered and the solution was added to an excess of MeOH. The copolymer product precipitated from solution and was filtered and washed with excess methanol. After drying to constant weight (overnight in a vacuum oven at 80° C.) the yield of copolymer amounted to 6.5 grams. Proton NMR confirmed the product to be a copolymer of ethylene and norbornene and the GPC data revealed the Mw to be 15,200 and the Mn 9,500. The glass transition temperature was determined to be 210° C. by DSC.

Polymerization Example 38

To a clean, dry 500 mL stainless steel reactor 40.0 g (425 mmol) of norbornene in 150 mL of dry, deoxygenated toluene was added under nitrogen. The reactor temperature was allowed to remain at ambient temperature and the stirred solution was saturated with ethylene. Bis(cycloctadiene)nickel(0) (0.244 g, 0.88 mmol) in toluene (4 mL) and hexafluoroacetylacetone (0.14 mL, 1.0 mmol) were premixed at ambient temperature for 10 minutes and then added to the reactor. The reactor was then pressurized to 400 psig with ethylene. The reaction was allowed to proceed 1 hour at which time the ethylene pressure was vented, the reactor was lowered and the solution was added to an excess of MeOH. The copolymer product precipitated from solution and was filtered and washed with excess methanol. After drying to constant weight (overnight in a vacuum oven at 80° C.) the yield of copolymer amounted to 2.14 grams. Proton NMR confirmed the product to be a copolymer of ethylene and norbornene (77 mole percent norbornene and 23 mole percent ethylene) and the GPC data revealed the Mw to. be 15,700 and the Mn 6,500. The glass transition temperature was determined to be 192° C. by DSC.

Polymerization Example 39

To a clean, dry 80 mL stainless steel reactor 0.0409 g. (0.149 mmol) of bis(cyclooctadiene)nickel was added under argon followed by 2 mL of dry, deoxygenated toluene. Then 0.0472 g. (0.148 mmol) of acetylmethylenetriphenylphosphoran (Fluka) and 2 mL of toluene were introduced and after several minutes of stirring 40 mL of 0.702 g/mL toluene solution of norbornene (total 0.3 mol; NB/Ni mole ratio~2000) was added. The reactor was then pressurized to 10 atm. (~140 psig) with ethylene. The reaction was allowed to proceed 70 h at which time the ethylene pressure (dropped to~5 atm.)—was vented and the solution was poured into excess of methanol. The polymer was subsequently filtered and dried in a vacuum overnight. The yield was 14 g.; $M_w$=144,000 and $M_n$=65,200. The incorporation of ethylene was determined to be 57 mole percent by NMR spectroscopy. Glass transition temperature (DSC) was 138° C.

Polymerzation Example 40

To a clean, dry 80 mL stainless steel reactor 0.025 g. (0.091 mmol) of bis(cyclooctadiene)nickel was added under argon followed by 2 mL of dry, deoxygenated toluene. Then 0.0289 g. (0.091 mmol) of acetylmethylenetriphenylphosphoran and 2 mL of toluene were introduced and after several minutes of stirring 36.5 mL toluene solution of norbornene (total 0.272 mol; NB/Ni mole ratio~3000) was added. The reactor was then pressurized to 14 at (~200 psig) with ethylene. The reaction was allowed to proceed 20 h at which time the ethylene pressure (dropped to~9.5 at) was vented and the solution was poured into an excess of methanol. The resulting polymer was subsequently filtered and dried in a vacuum overnight. The yield was 13.75 g.; $M_w$=62,800 and $M_n$=22,000. The copolymer contained 59 mole percent of ethylene according to NMR spectroscopy. Glass transition temperature was determined to be 132° C. by DSC.

Polymerization Example 41

To clean, dry Schlenk tube 0.182 g. (0.393 mmol) of bis(cyclooctadiene)nickel and 0.125 g. of acetylmethylenetriphenylphosphoran were added under argon followed by 16 mL of dry, deoxygenated toluene. The concentration of the resulting solution was 0.0246 mmol/mL. Then 1.87 mL of this solution was introduced into an 80 mL reactor followed by the addition of 36.5 mL of 0.702 g/mL toluene solution of norbornene (total 0.272 mol NB; NB/Ni mole ratio 5900) was added. The reactor was then pressurized to 14 atm. (~200 psig) with ethylene. The reaction was allowed to proceed 40 h at which time the ethylene pressure was vented and the solution was poured into excess of methanol. The resulting polymer was subsequently filtered and dried in a vacuum overnight. The yield was 11.9 g.; $M_w$=134,600 and $M_n$=62,200. The incorporation of ethylene was determined to be ~60 mole percent by NMR spectroscopy. Glass transition temperature was determined to be 125° C. by DSC.

Polymerization Example 42

To the rest of the solution of complex {Ni[PPh$_2$=CHC(O)Me](Ph)} prepared in Example 41, 3.2 mL of 0.702 g./mL solution of norbornene in toluene was added. The clear yellow solution was kept for 5 days in a Schlenk tube. Then 5.2 mL of this solution (0.0486 mmol Ni) was introduced into a clean, dry 80 mL stainless steel reactor and 36.5 mL of 0.702 g./mL toluene solution of norbornene (total 0.297 mol; NB/Ni mole ratio 6100) was added. The reactor was then pressurized to 14 atm. (~200 psig) with ethylene. The reaction was allowed to proceed 72 h at which time the ethylene pressure was vented and the solution was poured into excess of methanol. The resulting polymer was subsequently filtered and dried in a vacuum overnight. The yield was 9.7 g.; $M_w$=39,250 and $M_n$=21,600. The incorporation of ethylene was determined to be 60 mole percent by NMR spectroscopy. Glass transition temperature was determined to be 126° C. by DSC.

Polymerization Example 43

In a dry 50 mL flask 0.2569 g. (0.935 mmol) of bis(cyclooctadiene)nickel and 9 mL of dry, deoxygenated toluene were introduced under argon and 0.160 g. (0.905 mmol) of N-isobutylsalicylaldimine in 9 mL of toluene was gradually added from dropping funnel. Red-brown solution was formed. After 6 h an abundant pale brown precipitated Toluene was distilled off and a part of precipitate was dissolved in 43 mL of hexane. Greenish solution obtained contained ~0.01 mmol Ni/mL. 8 mL of this solution and 2 g. (21.3 mmol) of norbornene [NB/Ni=266] in 2 mL of hexane were introduced in a reactor and the latter was pressurized to 3.7 atm. (53 psig) with ethylene. Then the reactor was placed in a thermostat at 80° C. for 4 h. After this was cooled, the ethylene pressure was vented and the solution was poured into excess of methanol to precipitate the polymer. The latter was filtered and dried in vacuum overnight. The yield of the copolymer was 0.16 g. and proton NMR revealed that the copolymer contained 56 mole percent of norbornene and 44 mole percent of ethylene units. DSC revealed the copolymer to exhibit two glass transition points at 135 and 183° C.

Polymerization Example 44

To a clean, dry 500 mL stainless steel reactor 20.0 g of norbornene in 150 mL of dry, deoxygenated toluene was added under nitrogen. The reactor temperature was allowed to remain at ambient temperature. To the reactor was added catalyst A (0.034 g, 0.048 mmol) in a minimum amount of toluene. The reactor was then pressurized to 100 psig with ethylene. The reaction was allowed to proceed 2 h at which time the ethylene pressure was vented, the reactor was lowered and the solution was poured into an excess of MeOH to precipitate the polymer which was subsequently filtered and dried in a vacuum oven overnight. The filtrate was allowed to evaporate and additional polymer was isolated. Yield 6.5 g. $M_w$4,000 and $M_n$=2,100. The incorporation of ethylene was determined to be approximately 46 mole percent by NMR spectroscopy.

Polymerization Example 45

To a clean, dry 500 miL stainless steel reactor 40.0 g of norbornene in 150 mL of dry, deoxygenated toluene was added under nitrogen. The reactor temperature was allowed to remain at ambient temperature and the reactor was saturated with ethylene. To the reactor was added bis(cyclooctadiene)nickel (0.244 g, 0.88 mmol) in toluene (4 mL.) followed by hexafluoroacetylacetone (0.14 mL, 1.0 mmol). The reactor was then pressurized to 250 psig with ethylene. The reaction was allowed to proceed 2 h at which time the ethylene pressure was vented, the reactor was lowered and the solution was poured into an excess of MeOH to precipitate the polymer which was subsequently filtered and dried in a vacuum oven overnight. The filtrate was allowed to evaporate and additional polymer was isolated. Yield 6.5 g. $M_w$=15,200 and $M_n$=9,500. The incorporation of ethylene was approximately 22 mole percent and of norbornene approximately 78 mole percent as determined by NMR spectroscopy. The copolymer exhibited a glass transition temperature of 210° C.

Polymerization Example 46

To a clean, dry 500 mL stainless steel reactor 40.0 g of norbornene in 150 mL of dry, deoxygenated toluene was added under nitrogen. The reactor temperature was allowed to remain at ambient temperature and the reactor was saturated with ethylene. To the reactor was added a mixture of bis(cyclooctadiene)nickel (0.244 g, 0.88 mmol) and hexafluoroacetylacetone (0.14 mL, 1.0 mmol) in toluene (2 mL.) Which had first been allowed to stand at 10 minutes. The reactor was then pressurized to 400 psig with ethylene. The reaction was allowed to proceed 2 h at which time the ethylene pressure was vented, the reactor was lowered and the solution was poured into an excess of MeOH to precipitate the polymer which was subsequently filtered and dried in a vacuum oven overnight. The filtrate was allowed to evaporate and additional polymer was isolated. Yield 2.14 g. $M_w$=17,700 and $M_n$=8,400. The incorporation of ethylene was approximately 26 mole percent and of norbornene approximately 74 mole percent as determined by NMR spectroscopy. The copolymer exhibited a glass transition temperature of 224° C.

Polymerization Examples 47–69

In the examples listed in the following table the procedure of Example 4 was followed. In every case catalyst C was employed. The amount of norbornene used is listed, and the norbornene was diluted to a total volume of 150 mL in the noted solvent. The molar ratio of norbornene to catalyst is listed as is the reaction temperature.

TABLE (Examples 47–69)

| Example # | Temp C. | Catalyst ratio (NB:Ni) | NB/Et g/psi | Solvent | Yield g | NB mol % in Copolymer | Mn | Mw | Tg C |
|---|---|---|---|---|---|---|---|---|---|
| 47 | RT | 2000:1 | 20/100 | Toluene | 6.81 | 44 | 30,179 | 60,883 | 110 |
| 48 | RT | 1000:1 | 20/100 | Toluene | 16.73 | 43 | | | |
| 49 | RT | 500:1 | 20/100 | Toluene | 23.42 | 44 | 25,193 | 50,488 | |
| 50 | RT | 4000:1 | 20/100 | Toluene | 3.3 | 47 | 33,644 | 66,500 | |
| 51 | 5 | 2000:1 | 20/100 | Toluene | 1.66 | 46 | 32,920 | 55,863 | |
| 52 | 10 | 2000:1 | 20/100 | Toluene | 3.78 | 44 | 37,478 | 74,834 | |
| 53 | 15 | 2000:1 | 20/100 | Toluene | 9.74 | 43 | 32,100 | 70,194 | |
| 54 | 20 | 2000:1 | 20/100 | Toluene | 8.1 | 44 | 41,541 | 80,915 | |
| 55 | 35 | 2000:1 | 20/100 | Toluene | 1.61 | 36 | 22,407 | 49,928 | |
| 56 | 45 | 2000:1 | 20/100 | Toluene | 1.15 | 51 | 17,677 | 48,878 | |
| 57 | RT | 2000:1 | 40/100 | Toluene | 15.74 | 48 | 29,036 | 74,795 | |
| 58 | RT | 2000:1 | 60/100 | Toluene | 20.16 | 49 | 38,965 | 85,755 | |
| 59 | RT | 2000:1 | 80/100 | Toluene | 23.25 | | 45,145 | 83,939 | |
| 60 | RT | 2000:1 | 100/100 | Toluene | 28.15 | | 42,765 | 78,695 | 135.1 |
| 61 | RT | 2000:1 | 20/50 | Toluene | 3.12 | 52 | 29,108 | 74,337 | |
| 62 | RT | 2000:1 | 20/150 | Toluene | 20 | 40 | 27,425 | 55,133 | 89.3 |
| 63 | RT | 2000:1 | 20/200 | Toluene | 28.43 | 33 | 21,370 | 44,716 | 60.4 |
| 64 | RT | 2000:1 | 20/300 | Toluene | 34.02 | 26 | 21,077 | 39,970 | 83.9; 32.1 |
| 65 | 15 | 2000:1 | 100/150 | Toluene | 56.25 | 48 | 40,310 | 85,577 | 122.5 |
| 66 | 20 | 2000:1 | 100/150 | Toluene | 50.8 | 47 | 38,907 | 75,986 | 126.3 |
| 67 | RT | 2000:1 | 100/150 | Toluene | 35.46 | 48 | 35,910 | 66,735 | 130.4 |
| 68 | RT | 2000:1 | 20/100 | Xylene | 8.8 | | 30,956 | 63,806 | |
| 69 | RT | 2000:1 | 20/100 | Mesitylene | 5.34 | | 41,785 | 85,192 | |

We claim:

1. A method of preparing a substantially amorphous copolymer from ethylene and at least one norbornene-type monomer having the structure

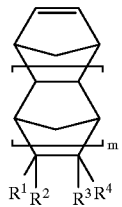

wherein $R^1$ to $R^4$ independently represents hydrogen, linear or branched ($C_1$–$C_{10}$) alkyl, aromatic or saturated or unsaturated cyclic groups; a functional substituent selected from the group consisting of —$(CH_2)_n$—C(O)OR, —$(CH_2)_n$—OR, —$(CH_2)_n$—OC(O)R, —$(CH_2)_n$—C(O)R and —$(CH_2)_n$—OC(O)OR, —$(CH_2)_nC(R)_2CH(R)(C(O)OR)$, —$(CH_2)_nC(R)_2CH(C(O)OR)_2$, wherein R represents hydrogen, or linear and branched ($C_1$ to $C_{10}$) alkyl; or a silyl substituent represented as follows:

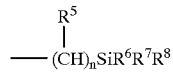

wherein $R^5$ independently represents hydrogen, methyl, or ethyl, $R^6$, $R^7$, and $R^8$ independently represent halogen selected from bromine, chlorine, fluorine, and iodine, linear or branched ($C_1$ to $C_{20}$) alkyl, linear or branched ($C_1$ to $C_{20}$) alkoxy, linear or branched ($C_1$ to $C_{20}$) alkyl carbonyloxy, linear or branched ($C_1$ to $C_{20}$) alkyl peroxy, substituted or unsubstituted ($C_6$ to $C_{20}$) aryloxy; any of $R^1$ and $R^2$ or $R^3$ and $R^4$ when taken together can form a ($C_1$ to $C_{10}$) alkylidenyl group;

m is an integer from 0 to 5;

n is an integer from 0 to 10;

$R^1$ and $R^4$, taken together with the two ring carbon atoms to which they are attached, represent a saturated cyclic group of 4 to 8 carbon atoms, wherein said cyclic group can be substituted by at least one of $R^2$ and $R^3$; said method comprising polymerizing said monomers in the presence of a neutral nickel catalyst represented by the formula

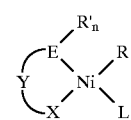

I wherein Y is a saturated or unsaturated hydrocarbyl chain containing 1 to 3 carbon atoms where two adjoining carbon atoms may form part of a cyclic structure X is O or S, E is P, As, Sb, N or O, R and R' independently is H or $C_{1-20}$ hydrocarbyl, n is 0, 1 or 2, and L is a ligand bearing the heteroatom P, N or O or alternatively R and L together form part of a chelating structure.

2. A method of claim 1, wherein

L is a weakly coordinating ligand;

E is phosphorus, each R and R' is independently an aryl or an alkyl group;

X is oxygen, and said polymerization is carried out in a diluent.

3. A method of claim 2, wherein L is a triphenylphosphine oxide or pyridine.

4. A method of claim 1 wherein the neutral nickel catalyst is a dinickel compound of the formula:

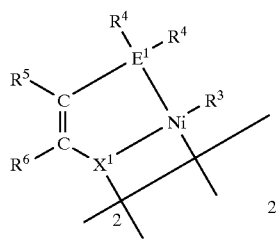

(II)

wherein $R^3$ and each $R^4$, independently, is H or $C_{1-20}$ hydrocarbyl;

$X^1$ is O or S;

$E^1$ is P, As or Sb; and $R^5$ and $R^6$, independently, is H, $C_{1-20}$ hydrocarbyl or a functional group selected from the group consisting of —$OR^2$, —Cl, —$CO_2R^2$, —$CO_2M$, —$C(O)N(R^1)_2$, —$C(O)R^2$, —$SR^2$, —$SO_2R^2$, —$SOR^2$, —O—$SO_2R^2$, —$P(O)(OR^2)_{2-y}(R^1)_y$, —CN, —$NHR^2$, —$N(R^2)_2$,

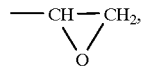

—$Si(OR^1)_{3-x}(R^1)_x$, —$OSi(OR^1)_{3-x}(R^1)x$, —$NO_2$, —$SO_3M$, —$PO_3M_2$ and —$P(O)(OR^2)_2M$, wherein M is alkali or alkaline earth metal, ammonium, quaternary ammonium, phosphonium or arsonium, y is 0, 1 or 2, each $R^1$, independently, is H or $C_{1-20}$ hydrocarbyl, each $R^2$, independently, is $C_{1-20}$ hydrocarbyl, and x is 0 or an integer of 1 to 3, or $R^5$ and $R^6$, taken together with the carbon atoms to which they are attached, is a substituted or unsubstituted $C_{5-8}$ alicyclic, $C_{5-8}$ heterocyclic or $C_{6-14}$ aromatic ring, the heteroatom of the heterocyclic ring being selected from O, N and S.

5. A method of claim 4 wherein $R^3$ is phenyl, pentafluorophenyl or methyl;

$R^4$ is phenyl, isopropyl or cyclohexyl;

$X^1$ is oxygen;

$E^1$ is phosphorus; and $R^5$ is hydrogen or the group —$SO_3M$ where M is sodium or potassium, $R^6$ is phenyl.

6. A method of claim 1 wherein the neutral nickel catalyst is a nickel compound of the formula

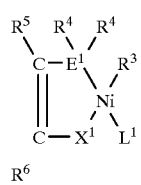

(III)

wherein:

$R^3$ and each $R^4$, independently, is H or $C_{1-20}$ hydrocarbyl;

$X^1$ is O or S;

$E^1$ is P, As or Sb; and $R^5$ and $R^6$, independently, is H, $C_{1-20}$ hydrocarbyl or a functional group selected from the group consisting of —$OR^2$, —Cl, —$CO_2R^2$, —$CO_2M$, —$C(O)N(R^1)_2$, —$C(O)R^2$, —$SR^2$, —$SO_2R^2$, —$SOR^2$, —O—$SO_2R^2$, —$P(O)(OR^2)_{2-y}(R^1)_y$, —CN, —$NHR^2$, —$N(R^2)_2$,

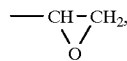

—$Si(OR^1)_{3-x}(R^1)_x$, —$OSi(OR^1)_{3-x}(R^1)x$, —$NO_2$, —$SO_3M$, —$P3O_2M$ and —$P(O)(OR^2)_2M$, wherein M is alkali or alkaline earth metal, ammonium, quaternary ammonium, phosphonium or arsonium, y is 0, 1 or 2, each $R^1$, independently, is H or $C_{1-20}$ hydrocarbyl, each $R^2$, independently, is $C_{1-20}$ hydrocarbyl, and x is 0 or an integer of 1 to 3, or $R^5$ and $R^6$, taken together with the carbon atoms to which they are attached, is a substituted or unsubstituted $C_{5-8}$ alicyclic, $C_{5-8}$ heterocyclic or $C_{6-14}$ aromatic ring, the heteroatom of the heterocyclic ring being selected from O, N and S; and $L^1$ is a weakly coordinating ligand, or $R^3$ and $L^1$ taken together form a group having the structure

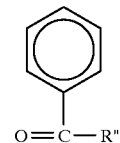

wherein R" is H, $C_{1-20}$ hydrocarbyl or oxyhydrocarbyl or $N(R^2)_2$ wherein each $R^2$, independently, is $C_{1-20}$ hydrocarbyl.

7. A method of claim 6 wherein $R^3$ is phenyl, pentafluorophenyl or methyl;

$R^4$ is phenyl, isopropyl or cyclohexyl;

$X^1$ is oxygen;

$E^1$ is phosphorus; and $R^5$ and $R^6$ independently are hydrogen or the group —$SO_3M$ where M is sodium or potassium; $L^1$ is a triphenylphosphine, triphenylphosphine methyleneylid or pyridine.

8. A method of claim 1 wherein the neutral nickel catalyst is a nickel compound of the formula

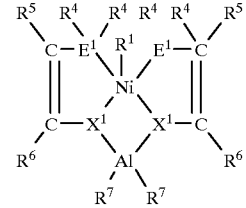

(IV)

wherein:

each $R^4$, independently, is H or $C_{1-20}$ hydrocarbyl;

$X^1$ is O or S;

$E^1$ is P, As or Sb; and $R^5$ and $R^6$, independently, is H, $C_{1-20}$ hydrocarbyl or a functional group selected from the group consisting of —$OR^2$, —Cl, —$CO_2R^2$, —$CO_2M$, —$C(O)N(R^1)_2$, —$C(O)R^2$, —$SR^2$, —$SO_2R^2$, —$SOR^2$, —O—$SO_2R^2$, —$P(O)(OR^2)_{2-y}(R^1)_y$, —CN, —$NHR^2$, —$N(R^2)_2$,

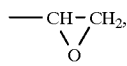

—Si(OR$^1$)$_{3-x}$(R$^1$)$_x$, —OSi(OR$^1$)$_{3-x}$(R$^1$)x, —NO$_2$, —SO$_3$M, —P3O$_2$M and P(O)(OR$^2$)$_2$M, wherein M is alkali or alkaline earth metal, ammonium, quaternary ammonium, phosphonium or arsonium, y is 0, 1 or 2, each R$^1$, independently, is H or C$_{1-20}$ hydrocarbyl, each R$^2$, independently, is C$_{1-20}$ hydrocarbyl, and x is 0 or an integer of 1 to 3, or R$^5$ and R$^6$, taken together with the carbon atoms to which they are attached, is a substituted or unsubstituted C$_{5-8}$ alicyclic, C$_{5-8}$ heterocyclic or C$_{6-14}$ aromatic ring, the heteroatom of the heterocyclic ring being selected from O, N and S;

R$^1$ and each R$^7$, independently, is H, —OSi(R'")$_3$, C$_{1-20}$ alkyl or oxyalkyl, C$_{6-20}$ aryl, alkaryl, aralkyl or oxyaryl, —N(R$^2$)$_2$ wherein R$^2$ is as defined above, or halogen, or both R$^7$ groups, taken together, is a 5 to 8-membered heterocyclic ring wherein the heteroatom is selected from O, N and S; and each R'", independently, is C$_{1-20}$ alkyl or oxyalkyl, C$_{6-20}$ aryl, alkaryl, aralkyl or oxyaryl.

9. A method of claim 8 wherein

E$^1$ is phosphorus;

X$^1$ is oxygen;

R$^4$ is phenyl, isopropyl or cyclohexyl;

R$^5$ is hydrogen or the group —SO$_3$M where M is sodium or potassium;

R$^6$ is phenyl; and each R$^1$ and R$^7$ is independently methyl, ethyl, isobutyl or octyl.

10. A method of claim 1 wherein the neutral nickel catalyst is a mixture comprising (i) a nickel compound of the formula

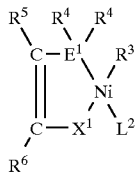

V wherein each R$^4$, independently, is H or C$_{1-20}$ hydrocarbyl;

X$^1$ is O or S;

E$^1$ is P, As or Sb;

L$^2$ is a strongly coordinating ligand; and

R$^5$ and R$^6$, independently, is H, C$_{1-20}$ hydrocarbyl or a functional group selected from the group consisting of —OR$^2$, —Cl, —CO$_2$R$^2$, —CO$_2$M, —C(O)N(R$^1$)$_2$, —C(O)R$^2$, —SR$^2$, —SO$_2$R$^2$, —SOR$^2$, —O—SO$_2$R$^2$, —P(O)(OR$^2$)$_{2-y}$(R$^1$)$_y$, —CN, —NHR$^2$, —N(R$^2$)$_2$,

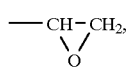

—Si(OR$^1$)$_{3-x}$(R$^1$)$_x$, —OSi(OR$^1$)$_{3-x}$(R$^1$)x, —NO$_2$, —SO$_3$M, —P3O$_2$M and —P(O)(OR$^2$)$_2$M, wherein M is alkali or alkaline earth metal, ammonium, quaternary ammonium, phosphonium or arsonium, y is 0, 1 or 2, each R$^1$, independently, is H or C$_{1-20}$ hydrocarbyl, each R$^2$, independently, is C$_{1-20}$ hydrocarbyl, and x is 0 or an integer of 1 to 3, or R$^5$ and R$^6$, taken together with the carbon atoms to which they are attached, is a substituted or unsubstituted C$_{5-8}$ alicyclic, C$_{5-8}$ heterocyclic or C$_{6-14}$ aromatic ring, the heteroatom of the heterocyclic ring being selected from O, N and S;

(ii) an acceptor compound which can react with L$^2$.

11. A method of claim 10 where

L$^2$ is a strongly coordinating ligand selected from phosphites and phosphines, and the acceptor compound is selected from nickel dicyclooctadiene, bis(ethylene) rhodium acetyl acetonate.

12. A method of claim 1 wherein the neutral nickel catalyst is a mixture comprising (i) a nickel compound of the formula

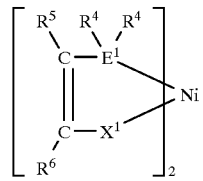

VI each R$^4$, independently, is H or C$_{1-20}$ hydrocarbyl;

X$^1$ is O or S;

E$^1$ is P, As or Sb; and

R$^5$ and R$^6$, independently, is H, C$_{1-20}$ hydrocarbyl or a functional group selected from the group consisting of —OR$^2$, —Cl, —CO$_2$R$^2$, —CO$_2$M, —C(O)N(R$^1$)$_2$, —C(O)R$^2$, —SR$^2$, —SO$_2$R$^2$, —SOR$^2$, —O—SO$_2$R$^2$, —P(O)(OR$^2$)$_{2-y}$(R$^1$)$_y$, —CN, —NHR$^2$, —N(R$^2$)$_2$,

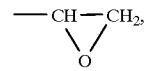

—Si(OR$^1$)$_{3-x}$(R$^1$)$_x$, —OSi(OR$^1$)$_{3-x}$(R$^1$)x, —NO$_2$, —SO$_3$M, —PO$_3$M$_2$ and —P(O)(OR$^2$)$_2$M, wherein M is alkali or alkaline earth metal, ammonium, quaternary ammonium, phosphonium or arsonium, y is 0, 1 or 2, each R$^1$, independently, is H or C$_{1-20}$ hydrocarbyl, each R$^2$, independently, is C$_{1-20}$ hydrocarbyl, and x is 0 or an integer of 1 to 3, or R$^5$ and R$^6$, taken together with the carbon atoms to which they are attached, is a substituted or unsubstituted C$_{5-8}$ alicyclic, C$_{5-8}$ heterocyclic or C$_{6-14}$ aromatic ring, the heteroatom of the heterocyclic ring being selected from O, N and S; and (ii) a suitable alkylating or arylating compound.

13. A method of claim 12, wherein

E$^1$ is phosphorus;

X$^1$ is oxygen;

each R$^4$ is independently phenyl, isopropyl or cyclohexyl;

R$^5$ is hydrogen or the group —SO$_3$M where M is sodium or potassium; and

R$^6$ is phenyl; and (ii) said alkylating or arylating compound is methyl iodide, ethyl iodide, phenyl iodide, trimethyl aluminum, triethyl aluminum, triisobutyl aluminum, triphenyl aluminum, dimethyl (1,5-cyclooctadiene) platinum (II), dimethyl bis(phosphine) nickel, or diphenyl bis(phosphine) nickel.

14. A method of preparing a substantially amorphous copolymer from ethylene and at least one norbornene-type monomer having the structure

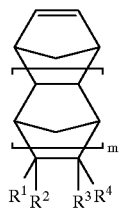

wherein $R^1$ to $R^4$ independently is a functional substituent selected from the group consisting of —$(CH_2)_n$—$C(O)OR$, —$(CH_2)_n$—$OR$, —$(CH_2)_n$—$OC(O)R$, —$(CH_2)_n$—$C(O)R$ and —$(CH_2)_n$—$OC(O)OR$, —$(CH_2)_nC(R)_2CH(R)(C(O)OR)$, —$(CH_2)_nC(R)_2CH(C(O)OR)_2$, wherein R represents hydrogen, or linear and branched ($C_1$ to $C_{10}$) alkyl; or a silyl substituent represented as follows:

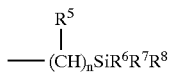

wherein $R^5$ independently represents hydrogen, methyl, or ethyl, $R^6$, $R^7$, and $R^8$ independently represent halogen selected from bromine, chlorine, fluorine, and iodine, linear or branched ($C_1$ to $C_{20}$) alkyl, linear or branched ($C_1$ to $C_{20}$) alkoxy, linear or branched ($C_1$ to $C_{20}$) alkyl carbonyloxy, linear or branched ($C_1$ to $C_{20}$) alkyl peroxy, substituted or unsubstituted ($C_6$ to $C_{20}$) aryloxy; any of $R^1$ and $R^2$ or $R^3$ and $R^4$ when taken together can form a ($C_1$ to $C_{10}$) alkylidenyl group;

m is an integer from 0 to 5;

n is an integer from 0 to 10;

$R^1$ and $R^4$, taken together with the two ring carbon atoms to which they are attached, represent a saturated cyclic group of 4 to 8 carbon atoms, wherein said cyclic group can be substituted by at least one of $R^2$ and $R^3$; said method comprising polymerizing said monomers in the presence of a neutral nickel catalyst represented by the formula

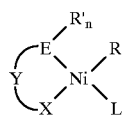

I wherein Y is a saturated or unsaturated hydrocarbyl chain containing 1 to 3 carbon atoms where two adjoining carbon atoms may form part of a cyclic structure X is O or S, E is P, As, Sb, N or O, R and R' independently is H or $C_{1-20}$ hydrocarbyl, n is 0, 1 or 2, and L is a ligand bearing the heteroatom P, N or O or alternatively R and L together form part of a chelating structure in which case L can be a C═C double bond.

15. A method of claim 14 wherein the functional substituent on the norbornene-type monomer is a silyl group.

16. A method of claim 15 wherein the silyl group is selected from trialkoxysilyl groups.

17. A method of claim 14 wherein the functional substituents are alkyl ester groups and acetate groups of NB-methanol.

18. A method of claim 1 wherein the catalyst is prepared in situ.

19. A method of claim 1 wherein the neutral nickel catalyst is a compound of the formula

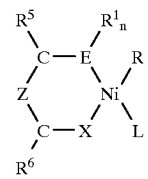

VII wherein Z is a double bond or a carbon atom containing one or two hydrogens or one or two $C_{1-20}$ hydrocarbyl groups provided that one or both hydrocarbyl groups can form a cyclic structure with the carbon atom adjoining Z;

$R^5$ and $R^6$, independently, each is H, $C_{1-20}$ hydrocarbyl or a functional group selected from the group consisting of —OR, —Cl, —$CO_2R^2$, —$CO_2M$, —$C(O)N(R^1)_2$, —$C(O)R^2$, —$SR^2$, —$SO_2R^2$, —$SOR^2$, —O—$SO_2R^2$, —$P(O)(OR^2)_{2-y}(R^1)_y$, —CN, —$NHR^2$, —$N(R^2)_2$,

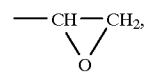

—$Si(OR^1)_{3-x}(R^1)_x$, —$OSi(OR^1)_{3-x}(R^1)_x$, —$NO_2$, —$SO_3M$, and —$P(O)(OR^2)_2M$, wherein M is alkali or alkaline earth metal, ammonium, quaternary ammonium, phosphonium or arsonium, y is 0, 1 or 2, each $R^1$, independently, is H or $C_{1-20}$ hydrocarbyl, each $R^2$, independently, is $C_{1-20}$ hydrocarbyl, and x is 0 or an integer of 1 to 3, or $R^5$ and $R^6$, taken together with the carbon atoms to which they are attached, is a substituted or unsubstituted $C_{5-8}$ alicyclic, $C_{5-8}$ heterocyclic or $C_{6-14}$ aromatic ring, the heteroatom of the heterocyclic ring being selected from O, N and S.

20. A method of claim 19 wherein the neutral nickel catalyst comprises of (a) a nickel compound where L is a strongly coordinating ligand, and (b) an acceptor compound that can react with or coordinate with ligand L.

21. A method of claim 19 where Z is a C═C double bond.

22. A method of claim 19 where Z is a hydrocarbyl group.

23. A method of claim 22 where said hydrocarbyl group contains a moiety —CH—, —CF—.

24. A method of claim 22 where Z is a hydrocarbyl group which, with the carbon atom adjoining Z, forms.

25. A method of copolymerizing ethylene and at least one norbornene-type monomer having the structure

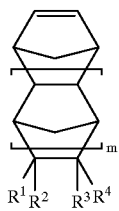

wherein $R^1$ to $R^4$ independently represents hydrogen, linear or branched ($C_1$–$C_{10}$) alkyl, aromatic or saturated or unsaturated cyclic groups; a functional substituent selected from the group consisting of —$(CH_2)_n$—$C(O)OR$, —$(CH_2)_n$—$OR$, —$(CH_2)_n$—$OC(O)R$, —$(CH_2)_n$—$C(O)R$ and —$(CH_2)_n$—$OC(O)OR$, —$(CH_2)_nC(R)_2CH(R)(C(O)OR)$, —$(CH_2)_nC(R)_2CH(C(O)OR)_2$, wherein R represents hydrogen, or linear and branched ($C_1$ to $C_{10}$) alkyl; or a silyl substituent represented as follows:

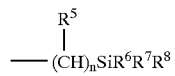

wherein $R^5$ independently represents hydrogen, methyl, or ethyl, $R^6$, $R^7$, and $R^8$ independently represent halogen selected from bromine, chlorine, fluorine, and iodine, linear or branched ($C_1$ to $C_{20}$) alkyl, linear or branched ($C_1$ to $C_{20}$) alkoxy, linear or branched ($C_1$ to $C_{20}$) alkyl carbonyloxy, linear or branched ($C_1$ to $C_{20}$) alkyl peroxy, substituted or unsubstituted ($C_6$ to $C_{20}$) aryloxy; any of $R^1$ and $R^2$ or $R^3$ and $R^4$ when taken together can form a ($C_1$ to $C_{10}$) alkylidenyl group;

m is an integer from 0 to 5;

n is an integer from 0 to 10;

$R^1$ and $R^4$, taken together with the two ring carbon atoms to which they are attached, represent a saturated cyclic group of 4 to 8 carbon atoms, wherein said cyclic group can be substituted by at least one of $R^2$ and $R^3$; said method comprising conducting the polymerization in the presence of a neutral nickel catalyst bearing a bidentate ligand which chelates the nickel via two hetero-atoms and a hydrocarbyl group.

26. A method of claim 25 wherein said norbornene-type monomer is a functional substituted norbornene.

* * * * *